US006218188B1

(12) United States Patent
Cardineau et al.

(10) Patent No.: US 6,218,188 B1
(45) Date of Patent: Apr. 17, 2001

(54) PLANT-OPTIMIZED GENES ENCODING PESTICIDAL TOXINS

(75) Inventors: Guy A. Cardineau, Poway; Steven J. Stelman; Kenneth E. Narva, both of San Diego, all of CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 09/178,252

(22) Filed: Oct. 23, 1998

Related U.S. Application Data

(60) Provisional application No. 60/076,445, filed on Mar. 2, 1998, and provisional application No. 60/065,215, filed on Nov. 12, 1997.

(51) Int. Cl.[7] ............................. C12N 1/21; C12N 5/14; C12N 15/00; C12N 15/32; C12N 15/82
(52) U.S. Cl. .................. 435/468; 435/252.3; 435/320.1; 435/449; 435/468; 536/23.71
(58) Field of Search ....................... 435/69.1, 320.1, 435/419, 468, 440, 252.3; 536/23.71; 800/279, 302

(56) References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 5,126,133 | 6/1992 | Payne et al. | 424/93 |
| 5,188,960 | 2/1993 | Payne et al. | 435/252.3 |
| 5,268,172 | 12/1993 | Payne et al. | 424/93 |
| 5,380,831 | 1/1995 | Adang et al. | 536/23.71 |
| 5,508,264 | 4/1996 | Bradfisch et al. | 514/12 |
| 5,527,883 | 6/1996 | Thompson et al. | 530/350 |
| 5,567,862 | 10/1996 | Adang et al. | 800/205 |
| 5,593,881 | 1/1997 | Thompson et al. | 435/240.1 |
| 5,723,758 | 3/1998 | Payne et al. | 800/205 |

FOREIGN PATENT DOCUMENTS

| | | |
|---|---|---|
| 9307278 | 4/1993 | (WO) . |
| 9405771 | 3/1994 | (WO) . |
| 9713402 | 3/1994 | (WO) . |
| 9506730 | 3/1995 | (WO) . |
| 9530753 | 11/1995 | (WO) . |
| 9534656 | 12/1995 | (WO) . |
| 9822595 | 5/1998 | (WO) . |

OTHER PUBLICATIONS

Ely, S., "The Engineering of Plants to Express *Bacillus thuringiensis* δ–Endotoxins," *Bacillus thuringiensis*, An Environmental Biopesticide: Theory and Practice, Entwistle et al., Ed. (1993 John Wiley & Sons, Ltd.).

Adang et al., GenBank Accession No. M11068, B. thuringiensis 75 kb plasmid crystal protein gene and flanks (Apr. 26, 1993).

Fujimoto, H., et al. (1993) "insect resistant rice generated by introduction of a modified delta–endotoxin gene of *Bacillus thuringiensis*" Bio/Technology 11(10):1151–1155.

Aronson, A.I., et al. (1991) "the Solubility of Inclusion Proteins from *Bacillus thuringiensis* Is Dependent upon Protoxin Composition and is a Factor in Toxicity to Insects" Applied and Environmental Microbiology 57(4):981–986.

Arvidson, H., et al. (1989) "Specificity of *Bacillus thuringiensis* for Lepidopteran Larvae: Factors Involved in vivo and in the Structure of Purified Toxin" Molecular Microbiology 3(11):1533–1543.

Choma, C.T., et al. (1990) "Unusual Proteolysis of the Toxin and Toxin from *Bacillus thuringiensis* Structural Implications" Eur. J. Biochem. 189, 523–527.

Crickmore, N., et al. (1996) Society for Invertebrate Pathology at the 29th Annual Meeting, the 3rd International Colloquium on *Bacillus thuringiensis* and the University of Cordoba. Sep. 1–6, 1996. Abstract.

Feitelson, J.S., et al. (1992) "*Bacillus thuringiensis* : Insects and Beyond" Bio/Technology 10:271–275.

Gaertner, F.H., L. KIm (1988) "Current Applied Recombinant DNA Projects" TIBTECH 6(4):S4–S7.

Gaertner, F.H. (1989) "Cellular Delivery Systems for Insecticidal Proteins: Living and Non–Living Microorganisms" in *Controlled Delivery of Crop–Protection Agents*, R.M. Wilkins, ed., Taylor and Francis, New York and London, 1990, pp. 245–255.

Haider, M.Z., et al. (1986) "Specificity of *Bacillus thuringiensis* var. colmeri Insecticidal δ–Endotoxins is Determined by Differential Proteolytic Processing of the Protoxin by Larval Gut Proteases" Eur. J. Biochem. 156,531–540.

Hofte, H., H.R. Whiteley (1989) "Insecticidal Crystal Proteins of *Bacillus thuringiensis* " Microbiological Reviews 53(2):242–255.

Li, Jade, et al. (1991) "Crystal Structure of Insecticidal δ–Endotoxin from *Bacillus thuringiensis* at 2.5 ÅResolution" Nature 353:815–821.

Schnepf, H.E., H.R. Whiteley (1981) "Cloning and Expression of the *Bacillus thuringiensis* Crystal Protein Gene in *Escherichia coli* " Proc. Natl. Acad. Sci. USA 78(5):2893–2897.

*Primary Examiner*—Amy J. Nelson
(74) *Attorney, Agent, or Firm*—Saliwanchik, Lloyd & Saliwanchik

(57) ABSTRACT

The subject invention concerns materials and methods useful in the control of pests and, particularly, plant pests. More specifically, the subject invention provides plant-optimized, polynucleotide sequences that encode pesticidal toxins (full-lengthand truncated). Truncated polynucleotide sequences can be used to produce truncated toxins or for the production of fusion (or chimeric) genes and proteins. The polynucleotide sequences of the subject invention have certain modifications, compared to wild-type sequences, that make them particularly well-suited for optimized expression in plants. Using techniques known to those skilled in the art, the polynucleotide sequences described herein can be used to transform plants in order to confer pest resistance upon the plants.

17 Claims, No Drawings

SEQUENCE LISTING

```
<160> NUMBER OF SEQ ID NOS: 27

<210> SEQ ID NO 1
<211> LENGTH: 3444
<212> TYPE: DNA
<213> ORGANISM: Artificial Sequence
<220> FEATURE:
<223> OTHER INFORMATION: Synthetic B.t. toxin gene

<400> SEQUENCE: 1
atggagaaca acatacagaa tcagtgcgtc ccctacaact gcctcaacaa tcctgaagta     60
gagattctca acgaagagag gtcgactggc agattgccgt tagacatctc cctgtccctt    120
acacgtttcc tgttgtctga gtttgttcca ggtgtgggag ttgcgtttgg cctcttcgac    180
ctcatctggg gcttcatcac tccatctgat tggagcctct ttcttctcca gattgaacag    240
ttgattgaac aaaggattga gaccttggaa aggaatcggg ccatcactac ccttcgtggc    300
ttagcagaca gctatgagat ctacattgaa gcactaagag agtgggaagc caatcctaac    360
aatgcccaac tgagagaaga tgtgcgtata cgctttgcta acacagatga tgctttgatc    420
acagccatca acaacttcac ccttaccagc ttcgagatcc ctcttctctc ggtctatgtt    480
caagctgcta acctgcactt gtcactactg cgcgacgctg tgtcgtttgg gcaaggttgg    540
ggactggaca tagctactgt caacaatcac tacaacagac tcatcaatct gattcatcga    600
```

| | |
|---|---|
| tacacgaaac attgtttgga tacctacaat cagggattgg agaacctgag aggtactaac | 660 |
| actcgccaat gggccaggtt caatcagttc aggagagacc ttacacttac tgtgttagac | 720 |
| atagttgctc tctttccgaa ctacgatgtt cgtacctatc cgattcaaac gtcatcccaa | 780 |
| cttacaaggg agatctacac cagttcagtc attgaagact ctccagtttc tgcgaacata | 840 |
| cccaatggtt tcaacagggc tgagtttgga gtcagaccac cccatctcat ggacttcatg | 900 |
| aactctttgt ttgtgactgc agagactgtt agatcccaaa ctgtgtgggg aggacactta | 960 |
| gttagctcac gcaacacggc tggcaatcgt atcaactttc ctagttacgg ggtcttcaat | 1020 |
| cccgggggcg ccatctggat tgcagatgaa gatccacgtc ctttctatcg gaccttgtca | 1080 |
| gatcctgtct tcgtccgagg aggctttggc aatcctcact atgtactcgg tcttagggga | 1140 |
| gtggcctttc aacaaactgg tacgaatcac acccgcacat tcaggaactc cgggaccatt | 1200 |
| gactctctag atgagatacc acctcaagac aacagcggcg caccttggaa tgactactcc | 1260 |
| catgtgctga atcatgttac ctttgtgcgc tggccaggtg agatctcagg ttccgactca | 1320 |
| tggagagcac caatgttctc ttggacgcat cgtagcgcta cccccacaaa caccattgat | 1380 |
| ccagagagaa tcactcagat tcccttggtg aaggcacaca cacttcagtc aggaactaca | 1440 |
| gttgtaagag ggccggggtt cacgggagga gacattcttc gacgcactag tggaggacca | 1500 |
| ttcgcgtaca ccattgtcaa catcaatggg caacttcccc aaaggtatcg tgccaggata | 1560 |
| cgctatgcct ctactaccaa tctaagaatc tacgttacgg ttgcaggtga acggatcttt | 1620 |
| gctggtcagt tcaacaagac aatggatacc ggtgatccac ttacattcca atctttctcc | 1680 |
| tacgccacta tcaacaccgc gttcaccttt ccaatgagcc agagcagttt cacagtaggt | 1740 |
| gctgatacct tcagttcagg caacgaagtg tacattgaca ggtttgagtt gattccagtt | 1800 |
| actgccacac tcgaggcaga gtctgacttg gaaagagcac agaaggcggt gaatgctctg | 1860 |
| ttcacttcgt ccaatcagat tgggctcaag acagatgtga ctgactatca catcgatcgc | 1920 |
| gtttccaacc ttgttgagtg cctctctgat gagttctgtt tggatgagaa gaaggagttg | 1980 |
| tccgagaagg tcaaacatgc taagcgactt agtgatgagc ggaacttgct tcaagatccc | 2040 |
| aactttcgcg ggatcaacag gcaactagat cgtggatgga ggggaagtac ggacatcacc | 2100 |
| attcaaggag gtgatgatgt gttcaaggag aactatgtta cgctcttggg taccttttgat | 2160 |
| gagtgctatc caacatacct gtaccagaag atagatgaat cgaaactcaa agcctacaca | 2220 |
| agataccagt tgagaggtta tcgaggac agtcaagacc ttgagatcta cctcatcaga | 2280 |
| tacaacgcca acatgagaca agtcaatgtg cctgggacgg gttcactctg gccactttca | 2340 |
| gccccaagtc ccatcggcaa gtgtgcccat cactcacacc acttctcctt ggacatagac | 2400 |
| gttggctgta ccgacctgaa cgaagacctc ggtgtgtggg tgatcttcaa gatcaagact | 2460 |
| caagatggcc atgccaggct aggcaatctg gagtttctag aagagaaacc acttgttgga | 2520 |
| gaagccctcg ctagagtgaa gagggctgag aagaagtgga gggacaagag agagaagttg | 2580 |
| gaatgggaaa caaacattgt gtacaaagaa gccaaagaaa gcgttgacgc tctgtttgtg | 2640 |
| aactctcagt atgataggct ccaagctgat accaacatag ctatgattca tgctgcagac | 2700 |
| aaacgcgttc atagcattcg ggaagcttac cttcctgaac ttagcgtgat tccgggtgtc | 2760 |
| aatgctgcta tctttgaaga gttagaaggg cgcatcttca ctgcattctc cttgtatgat | 2820 |
| gcgaggaatg tcatcaagaa tggtgacttc aacaatggcc tatcctgctg gaatgtgaaa | 2880 |
| gggcacgtag atgtagaaga acagaacaat caccgctctg tccttgttgt tcctgagtgg | 2940 |
| gaagcagaag tttcacaaga agttcgtgtc tgtcctggtc gtggctacat tcttcgtgtt | 3000 |

-continued

```
accgcgtaca aagaaggata cggagaaggt tgcgtcacca tacacgagat tgagaacaac      3060
accgacgagc tgaagttcag caactgcgtc gaggaggaag tctacccaaa caacaccgta      3120
acttgcaatg actacactgc gactcaagag gagtatgagg gtacttacac ttctcgcaat      3180
cgaggatacg atggagccta tgagagcaac tcttctgtac ccgctgacta tgcatcagcc      3240
tatgaggaga aggcttacac cgatggacgt agggacaatc cttgcgaatc taacagaggc      3300
tatggggact acacaccgtt accagccggc tatgtcacca agagttaga gtactttcca      3360 gaaaccgaca aggtttggat tgagattgga gaaacggaag gaacattcat tgttgatagc      3420
gtggagttac ttctgatgga ggaa                                             3444
```

<210> SEQ ID NO 2
<211> LENGTH: 1148
<212> TYPE: PRT
<213> ORGANISM: Artificial Sequence
<220> FEATURE:
<223> OTHER INFORMATION: Toxin encoded by synthetic B.t. gene

<400> SEQUENCE: 2

```
Met Glu Asn Asn Ile Gln Asn Gln Cys Val Pro Tyr Asn Cys Leu Asn
  1               5                  10                  15

Asn Pro Glu Val Glu Ile Leu Asn Glu Glu Arg Ser Thr Gly Arg Leu
             20                  25                  30

Pro Leu Asp Ile Ser Leu Ser Leu Thr Arg Phe Leu Leu Ser Glu Phe
         35                  40                  45

Val Pro Gly Val Gly Val Ala Phe Gly Leu Phe Asp Leu Ile Trp Gly
     50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
```

```
                275                 280                 285
Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
                340                 345                 350

Arg Pro Phe Tyr Arg Thr Leu Ser Asp Pro Val Phe Val Arg Gly Gly
            355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
                420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
                500                 505                 510

Pro Gln Arg Tyr Arg Ala Arg Ile Arg Tyr Ala Ser Thr Thr Asn Leu
            515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
                580                 585                 590

Asp Arg Phe Glu Leu Ile Pro Val Thr Ala Thr Leu Glu Ala Glu Ser
            595                 600                 605

Asp Leu Glu Arg Ala Gln Lys Ala Val Asn Ala Leu Phe Thr Ser Ser
    610                 615                 620

Asn Gln Ile Gly Leu Lys Thr Asp Val Thr Asp Tyr His Ile Asp Arg
625                 630                 635                 640

Val Ser Asn Leu Val Glu Cys Leu Ser Asp Glu Phe Cys Leu Asp Glu
                645                 650                 655

Lys Lys Glu Leu Ser Glu Lys Val Lys His Ala Lys Arg Leu Ser Asp
                660                 665                 670

Glu Arg Asn Leu Leu Gln Asp Pro Asn Phe Arg Gly Ile Asn Arg Gln
            675                 680                 685

Leu Asp Arg Gly Trp Arg Gly Ser Thr Asp Ile Thr Ile Gln Gly Gly
    690                 695                 700
```

```
Asp Asp Val Phe Lys Glu Asn Tyr Val Thr Leu Leu Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Tyr Thr Arg Tyr Gln Leu Arg Gly Tyr Ile Glu Asp Ser Gln
                740                 745                 750

Asp Leu Glu Ile Tyr Leu Ile Arg Tyr Asn Ala Lys His Glu Thr Val
            755                 760             765

Asn Val Pro Gly Thr Gly Ser Leu Trp Pro Leu Ser Ala Pro Ser Pro
        770                 775             780

Ile Gly Lys Cys Ala His His Ser His His Phe Ser Leu Asp Ile Asp
785             790             795                 800

Val Gly Cys Thr Asp Leu Asn Glu Asp Leu Gly Val Trp Val Ile Phe
                805             810                 815

Lys Ile Lys Thr Gln Asp Gly His Ala Arg Leu Gly Asn Leu Glu Phe
                820             825             830

Leu Glu Glu Lys Pro Leu Val Gly Glu Ala Leu Ala Arg Val Lys Arg
            835             840             845

Ala Glu Lys Lys Trp Arg Asp Lys Arg Glu Lys Leu Glu Trp Glu Thr
        850             855             860

Asn Ile Val Tyr Lys Glu Ala Lys Glu Ser Val Asp Ala Leu Phe Val
865             870             875                 880

Asn Ser Gln Tyr Asp Arg Leu Gln Ala Asp Thr Asn Ile Ala Met Ile
                885             890                 895

His Ala Ala Asp Lys Arg Val His Ser Ile Arg Glu Ala Tyr Leu Pro
            900             905             910

Glu Leu Ser Val Ile Pro Gly Val Asn Ala Ala Ile Phe Glu Glu Leu
        915             920             925

Glu Gly Arg Ile Phe Thr Ala Phe Ser Leu Tyr Asp Ala Arg Asn Val
        930             935             940

Ile Lys Asn Gly Asp Phe Asn Asn Gly Leu Ser Cys Trp Asn Val Lys
945             950             955             960

Gly His Val Asp Val Glu Glu Gln Asn Asn His Arg Ser Val Leu Val
                965             970             975

Val Pro Glu Trp Glu Ala Glu Val Ser Gln Glu Val Arg Val Cys Pro
            980             985             990

Gly Arg Gly Tyr Ile Leu Arg Val Thr Ala Tyr Lys Glu Gly Tyr Gly
        995             1000            1005

Glu Gly Cys Val Thr Ile His Glu Ile Glu Asn Asn Thr Asp Glu Leu
    1010            1015            1020

Lys Phe Ser Asn Cys Val Glu Glu Val Tyr Pro Asn Asn Thr Val
1025            1030            1035            1040

Thr Cys Asn Asp Tyr Thr Ala Thr Gln Glu Glu Tyr Glu Gly Thr Tyr
                1045            1050            1055

Thr Ser Arg Asn Arg Gly Tyr Asp Gly Ala Tyr Glu Ser Asn Ser Ser
            1060            1065            1070

Val Pro Ala Asp Tyr Ala Ser Ala Tyr Glu Glu Lys Ala Tyr Thr Asp
            1075            1080            1085

Gly Arg Arg Asp Asn Pro Cys Glu Ser Asn Arg Gly Tyr Gly Asp Tyr
        1090            1095            1100

Thr Pro Leu Pro Ala Gly Tyr Val Thr Lys Glu Leu Glu Tyr Phe Pro
1105            1110            1115            1120
```

Glu Thr Asp Lys Val Trp Ile Glu Ile Gly Glu Thr Glu Gly Thr Phe
            1125                1130                1135

Ile Val Asp Ser Val Glu Leu Leu Leu Met Glu Glu
            1140                1145

<210> SEQ ID NO 3
<211> LENGTH: 1815
<212> TYPE: DNA
<213> ORGANISM: Artificial Sequence
<220> FEATURE:
<223> OTHER INFORMATION: Synthetic B.t. toxin gene

<400> SEQUENCE: 3

| | | |
|---|---|---|
| atggagaaca acatacagaa tcagtgcgtc ccctacaact gcctcaacaa tcctgaagta | 60 |
| gagattctca acgaagagag gtcgactggc agattgccgt tagacatctc cctgtccctt | 120 |
| acacgtttcc tgttgtctga gtttgttcca ggtgtgggag ttgcgtttgg cctcttcgac | 180 |
| ctcatctggg gcttcatcac tccatctgat tggagcctct tcttctcca gattgaacag | 240 |
| ttgattgaac aaaggattga gaccttggaa aggaatcggg ccatcactac ccttcgtggc | 300 |
| ttagcagaca gctatgagat ctacattgaa gcactaagag agtgggaagc caatcctaac | 360 |
| aatgcccaac tgagagaaga tgtgcgtata cgctttgcta acacagatga tgctttgatc | 420 |
| acagccatca acaacttcac ccttaccagc ttcgagatcc ctcttctctc ggtctatgtt | 480 |
| caagctgcta acctgcactt gtcactactg cgcgacgctg tgtcgtttgg caaggttgg | 540 |
| ggactggaca tagctactgt caacaatcac tacaacagac tcatcaatct gattcatcga | 600 |
| tacacgaaac attgtttgga tacctacaat cagggattgg agaacctgag aggtactaac | 660 |
| actcgccaat gggccaggtt caatcagttc aggagagacc ttacacttac tgtgttagac | 720 |
| atagttgctc tctttccgaa ctacgatgtt cgtacctatc cgattcaaac gtcatcccaa | 780 |
| cttacaaggg agatctacac cagttcagtc attgaagact ctccagtttc tgcgaacata | 840 |
| cccaatggtt tcaacaggc tgagtttgga gtcagaccac cccatctcat ggacttcatg | 900 |
| aactcttttg ttgtgactgc agagactgtt agatcccaaa ctgtgtgggg aggacactta | 960 |
| gttagctcac gcaacacggc tggcaatcgt atcaactttc ctagttacgg ggtcttcaat | 1020 |
| cccgggggcg ccatctggat tgcagatgaa gatccacgtc ctttctatcg gaccttgtca | 1080 |
| gatcctgtct tcgtccgagg aggctttggc aatcctcact atgtactcgg tcttagggga | 1140 |
| gtggcctttc aacaaactgg tacgaatcac acccgcacat tcaggaactc cgggaccatt | 1200 |
| gactctctag atgagatacc acctcaagac aacagcggcg caccttggaa tgactactcc | 1260 |
| catgtgctga atcatgttac ctttgtgcgc tggccaggtg agatctcagg ttccgactca | 1320 |
| tggagagcac caatgttctc ttggacgcat cgtagcgcta cccccacaaa caccattgat | 1380 |
| ccagagagaa tcactcagat tcccttggtg aaggcacaca cacttcagtc aggaactaca | 1440 |
| gttgtaagag ggccggggtt cacgggagga gacattcttc gacgcactag tggaggacca | 1500 |
| ttcgcgtaca ccattgtcaa catcaatggg caacttcccc aaaggtatcg tgccaggata | 1560 |
| cgctatgcct ctactaccaa tctaagaatc tacgttacgg ttgcaggtga acggatcttt | 1620 |
| gctggtcagt tcaacaagac aatggataca ggtgatccac ttacattcca atctttctcc | 1680 |
| tacgccacta tcaacaccgc gttcaccttt ccaatgagcc agagcagttt cacagtaggt | 1740 |
| gctgatacct tcagttcagg caacgaagtg tacattgaca ggtttgagtt gattccagtt | 1800 |
| actgccacac tcgag | 1815 |

```
<210> SEQ ID NO 4
<211> LENGTH: 605
<212> TYPE: PRT
<213> ORGANISM: Artificial Sequence
<220> FEATURE:
<223> OTHER INFORMATION: Toxin encoded by synthetic B.t. gene

<400> SEQUENCE: 4
```

Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln

|     |     |     |     |     | 370 |     |     |     |     | 375 |     |     |     |     | 380 |     |     |     |     |
| --- | --- | --- | --- | --- | --- | --- | --- | --- | --- | --- | --- | --- | --- | --- | --- | --- | --- | --- | --- |
| Gln | Thr | Gly | Thr | Asn | His | Thr | Arg | Thr | Phe | Arg | Asn | Ser | Gly | Thr | Ile |
| 385 |     |     |     |     | 390 |     |     |     |     | 395 |     |     |     |     | 400 |
| Asp | Ser | Leu | Asp | Glu | Ile | Pro | Pro | Gln | Asp | Asn | Ser | Gly | Ala | Pro | Trp |
|     |     |     |     | 405 |     |     |     |     | 410 |     |     |     |     | 415 |     |
| Asn | Asp | Tyr | Ser | His | Val | Leu | Asn | His | Val | Thr | Phe | Val | Arg | Trp | Pro |
|     |     |     | 420 |     |     |     |     | 425 |     |     |     |     | 430 |     |     |
| Gly | Glu | Ile | Ser | Gly | Ser | Asp | Ser | Trp | Arg | Ala | Pro | Met | Phe | Ser | Trp |
|     |     |     | 435 |     |     |     |     | 440 |     |     |     |     | 445 |     |     |
| Thr | His | Arg | Ser | Ala | Thr | Pro | Thr | Asn | Thr | Ile | Asp | Pro | Glu | Arg | Ile |
|     | 450 |     |     |     |     | 455 |     |     |     |     | 460 |     |     |     |     |
| Thr | Gln | Ile | Pro | Leu | Val | Lys | Ala | His | Thr | Leu | Gln | Ser | Gly | Thr | Thr |
| 465 |     |     |     |     | 470 |     |     |     |     | 475 |     |     |     |     | 480 |
| Val | Val | Arg | Gly | Pro | Gly | Phe | Thr | Gly | Gly | Asp | Ile | Leu | Arg | Arg | Thr |
|     |     |     |     | 485 |     |     |     |     | 490 |     |     |     |     | 495 |     |
| Ser | Gly | Gly | Pro | Phe | Ala | Tyr | Thr | Ile | Val | Asn | Ile | Asn | Gly | Gln | Leu |
|     |     |     |     | 500 |     |     |     |     | 505 |     |     |     |     | 510 |     |
| Pro | Gln | Arg | Tyr | Arg | Ala | Arg | Ile | Arg | Tyr | Ala | Ser | Thr | Thr | Asn | Leu |
|     |     |     | 515 |     |     |     |     | 520 |     |     |     |     | 525 |     |     |
| Arg | Ile | Tyr | Val | Thr | Val | Ala | Gly | Glu | Arg | Ile | Phe | Ala | Gly | Gln | Phe |
|     | 530 |     |     |     |     | 535 |     |     |     |     | 540 |     |     |     |     |
| Asn | Lys | Thr | Met | Asp | Thr | Gly | Asp | Pro | Leu | Thr | Phe | Gln | Ser | Phe | Ser |
| 545 |     |     |     |     | 550 |     |     |     |     | 555 |     |     |     |     | 560 |
| Tyr | Ala | Thr | Ile | Asn | Thr | Ala | Phe | Thr | Phe | Pro | Met | Ser | Gln | Ser | Ser |
|     |     |     |     | 565 |     |     |     |     | 570 |     |     |     |     | 575 |     |
| Phe | Thr | Val | Gly | Ala | Asp | Thr | Phe | Ser | Ser | Gly | Asn | Glu | Val | Tyr | Ile |
|     |     |     |     | 580 |     |     |     |     | 585 |     |     |     |     | 590 |     |
| Asp | Arg | Phe | Glu | Leu | Ile | Pro | Val | Thr | Ala | Thr | Leu | Glu |
|     |     |     | 595 |     |     |     |     | 600 |     |     |     |     | 605 |

<210> SEQ ID NO 5
<211> LENGTH: 3522
<212> TYPE: DNA
<213> ORGANISM: Bacillus thuringiensis

<400> SEQUENCE: 5

```
atggagaata atattcaaaa tcaatgcgta ccttacaatt gtttaaataa tcctgaagta

-continued

```
cctaatggtt ttaatagggc ggaatttgga gttagaccgc cccatcttat ggactttatg      900
aattctttgt tgtaactgc agagactgtt agaagtcaaa ctgtgtgggg aggacactta       960
gttagttcac gaaatacggc tggtaaccgt ataaatttcc ctagttacgg ggtcttcaat     1020
cctggtggcg ccatttggat tgcagatgag gatccacgtc cttttatcg gacattatca     1080
gatcctgttt tgtccgagg aggatttggg aatcctcatt atgtactggg gcttagggga     1140
gtagcatttc aacaaactgg tacgaaccac acccgaacat ttagaaatag tgggaccata    1200
gattctctag atgaaatccc acctcaggat aatagtgggg caccttggaa tgattatagt    1260
catgtattaa atcatgttac atttgtacga tggccaggtg agatttcagg aagtgattca    1320
tggagagctc caatgttttc ttggacgcac cgtagtgcaa cccctacaaa tacaattgat    1380
ccggagagga ttactcaaat accattggta aaagcacata cacttcagtc aggtactact   1440
gttgtaagag ggcccgggtt tacgggagga gatattcttc gacgaacaag tggaggacca   1500
tttgcttata ctattgttaa tataaatggg caattacccc aaaggtatcg tgcaagaata   1560
cgctatgcct ctactacaaa tctaagaatt tacgtaacgg ttgcaggtga acggattttt   1620
gctggtcaat ttaacaaaac aatggatacc ggtgacccat taacattcca atcttttagt   1680
tacgcaacta ttaatacagc ttttacattc ccaatgagcc agagtagttt cacagtaggt    1740
gctgatactt ttagttcagg gaatgaagtt tatatagaca gatttgaatt gattccagtt    1800
actgcaacat ttgaagcaga atatgattta aaaagagcac aaaaggcggt gaatgcgctg    1860
tttacttcta taaaccaaat agggataaaa acagatgtga cggattatca tattgatcaa   1920
gtatccaatt tagtggattg tttatcagat gaattttgtc tggatgaaaa gcgagaattg   1980
tccgagaaag tcaaacatgc gaagcgactc agtgatgagc ggaatttact tcaagatcca   2040
aacttcaaag gcatcaatag gcaactagac cgtggttgga gaggaagtac ggatatacc    2100
atccaaagag gagatgacgt attcaaagaa aattatgtca cactaccagg tacctttgat   2160
gagtgctatc caacgtattt atatcaaaaa atagatgagt cgaaattaaa accctatact   2220
cgttatcaat taagagggta tatcgaggat agtcaagact tagaaatcta tttgatccgc   2280
tataatgcaa aacacgaaac agtaaatgtg ctaggtacgg gttctttatg gccgcttttca  2340
gtccaaagtc caatcagaaa gtgtgagaga ccgaatcgat gcgcgccaca ccttgaatgg   2400
aatcctgatc tagattgttc ctgcagagac ggggaaaat gtgcacatca ttcgcatcat    2460
ttctccttgg acattgatgt tggatgtaca gacttaaatg gacttaga tgtatgggtg    2520
atattcaaga ttaagacgca agatggccat gcaagactag gaaatctaga gtttctcgaa   2580
gagaaaccat tagtcgggga agcactagct cgtgtgaaaa gagcagagaa aaatggaga    2640
gataaacgtg aaaattgga attggaaaca aatattgttt ataaagaggc aaaagaatct    2700
gtagatgctt tatttgtaaa ctctcaatat gatcaattac aagcggatac gaatattgcc   2760
atgattcatg cggcagataa acgtgttcat agaattcggg aagcgtatct tccagagtta   2820
tctgtgattc cgggtgtaaa tgtagacatt ttcgaagaat taaagggcg tattttcact    2880
gcattcttcc tatatgatgc gagaaatgtc attaaaaacg gtgatttcaa taatggctta   2940
tcatgctgga acgtgaaagg gcatgtagat gtagaagaac aaaacaacca ccgttcggtc   3000
cttgttgttc cggaatggga agcagaagtg tcacaagaag ttcgtgtctg tccgggtcgt   3060
ggctatatcc ttcgtgtcac agcgtacaag gagggatatg gagaaggttg cgtaaccatt   3120
catgagatcg agaacaatac agacgaactg aagtttagca actgcgtaga agaggaagtc   3180
```

```
tatccaaaca acacggtaac gtgtaatgat tatactgcaa atcaagaaga atacgggggt    3240
gcgtacactt cccgtaatcg tggatatgac gaaacttatg gaagcaattc ttctgtacca    3300
gctgattatg cgtcagtcta tgaagaaaaa tcgtatacag atggacgaag agacaatcct    3360
tgtgaatcta acagaggata tggggattac acaccactac cagctggcta tgtgacaaaa    3420
gaattagagt acttcccaga aaccgataag gtatggattg agatcggaga aacggaagga    3480
acattcatcg tggacagcgt ggaattactc cttatggagg aa                      3522
```

<210> SEQ ID NO 6
<211> LENGTH: 1174
<212> TYPE: PRT
<213> ORGANISM: Bacillus thuringiensis

<400> SEQUENCE: 6

```
Met Gl

```
Val Ser Ser Arg Asn Thr Ala Gly Asn Arg Ile Asn Phe Pro Ser Tyr
            325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
            355                 360                 365
Phe Gly Asn Pro His Tyr Val Leu Gly Leu Arg Gly Val Ala Phe Gln
            370                 375                 380
Gln Thr Gly Thr Asn His Thr Arg Thr Phe Arg Asn Ser Gly Thr Ile
385                 390                 395                 400
Asp Ser Leu Asp Glu Ile Pro Pro Gln Asp Asn Ser Gly Ala Pro Trp
            405                 410                 415
Asn Asp Tyr Ser His Val Leu Asn His Val Thr Phe Val Arg Trp Pro
            420                 425                 430
Gly Glu Ile Ser Gly Ser Asp Ser Trp Arg Ala Pro Met Phe Ser Trp
            435                 440                 445
Thr His Arg Ser Ala Thr Pro Thr Asn Thr Ile Asp Pro Glu Arg Ile
450                 455                 460
Thr Gln Ile Pro Leu Val Lys Ala His Thr Leu Gln Ser Gly Thr Thr
465                 470                 475                 480
Val Val Arg Gly Pro Gly Phe Thr Gly Gly Asp Ile Leu Arg Arg Thr
            485                 490                 495
Ser Gly Gly Pro Phe Ala Tyr Thr Ile Val Asn Ile Asn Gly Gln Leu
            500                 505                 510
Pro Gln Arg Tyr Arg Ala Arg Ile Arg Tyr Ala Ser Thr Thr Asn Leu
            515                 520                 525
Arg Ile Tyr Val Thr Val Ala Gly Glu Arg Ile Phe Ala Gly Gln Phe
            530                 535                 540
Asn Lys Thr Met Asp Thr Gly Asp Pro Leu Thr Phe Gln Ser Phe Ser
545                 550                 555                 560
Tyr Ala Thr Ile Asn Thr Ala Phe Thr Phe Pro Met Ser Gln Ser Ser
            565                 570                 575
Phe Thr Val Gly Ala Asp Thr Phe Ser Ser Gly Asn Glu Val Tyr Ile
            580                 585                 590
Asp Arg Phe Glu Leu Ile Pro Val Thr Ala Thr Phe Glu Ala Glu Tyr
            595                 600                 605
Asp Leu Glu Arg Ala Gln Lys Ala Val Asn Ala Leu Phe Thr Ser Ile
            610                 615                 620
Asn Gln Ile Gly Ile Lys Thr Asp Val Thr Asp Tyr His Ile Asp Gln
625                 630                 635                 640
Val Ser Asn Leu Val Asp Cys Leu Ser Asp Glu Phe Cys Leu Asp Glu
            645                 650                 655
Lys Arg Glu Leu Ser Glu Lys Val Lys His Ala Lys Arg Leu Ser Asp
            660                 665                 670
Glu Arg Asn Leu Leu Gln Asp Pro Asn Phe Lys Gly Ile Asn Arg Gln
            675                 680                 685
Leu Asp Arg Gly Trp Arg Gly Ser Thr Asp Ile Thr Ile Gln Arg Gly
690                 695                 700
Asp Asp Val Phe Lys Glu Asn Tyr Val Thr Leu Pro Gly Thr Phe Asp
705                 710                 715                 720
Glu Cys Tyr Pro Thr Tyr Leu Tyr Gln Lys Ile Asp Glu Ser Lys Leu
            725                 730                 735
```

-continued

```
Lys Pro Tyr Thr Arg Tyr Gln Leu Arg Gly Tyr Ile Glu Asp Ser Gln
            740                 745                 750
Asp Leu Glu Ile Tyr Leu Ile Arg Tyr Asn Ala Lys His Glu Thr Val
            755                 760             765
Asn Val Leu Gly Thr Gly Ser Leu Trp Pro Leu Ser Val Gln Ser Pro
770             775                 780
Ile Arg Lys Cys Gly Glu Pro Asn Arg Cys Ala Pro His Leu Glu Trp
785                 790                 795                 800
Asn Pro Asp Leu Asp Cys Ser Cys Arg Asp Gly Glu Lys Cys Ala His
                805                 810                 815
His Ser His His Phe Ser Leu Asp Ile Asp Val Gly Cys Thr Asp Leu
                820                 825                 830
Asn Glu Asp Leu Asp Val Trp Val Ile Phe Lys Ile Lys Thr Gln Asp
            835                 840                 845
Gly His Ala Arg Leu Gly Asn Leu Glu Phe Leu Glu Glu Lys Pro Leu
850                 855                 860
Val Gly Glu Ala Leu Ala Arg Val Lys Arg Ala Glu Lys Lys Trp Arg
865                 870                 875                 880
Asp Lys Arg Glu Lys Leu Glu Leu Glu Thr Asn Ile Val Tyr Lys Glu
                885                 890                 895
Ala Lys Glu Ser Val Asp Ala Leu Phe Val Asn Ser Gln Tyr Asp Gln
            900                 905                 910
Leu Gln Ala Asp Thr Asn Ile Ala Met Ile His Ala Ala Asp Lys Arg
            915                 920                 925
Val His Arg Ile Arg Glu Ala Tyr Leu Pro Glu Leu Ser Val Ile Pro
        930                 935                 940
Gly Val Asn Val Asp Ile Phe Glu Glu Leu Lys Gly Arg Ile Phe Thr
945                 950                 955                 960
Ala Phe Phe Leu Tyr Asp Ala Arg Asn Val Ile Lys Asn Gly Asp Phe
                965                 970                 975
Asn Asn Gly Leu Ser Cys Trp Asn Val Lys Gly His Val Asp Val Glu
            980                 985                 990
Glu Gln Asn Asn His Arg Ser Val Leu Val Val Pro Glu Trp Glu Ala
        995                 1000                1005
Glu Val Ser Gln Glu Val Arg Val Cys Pro Gly Arg Gly Tyr Ile Leu
    1010                1015                1020
Arg Val Thr Ala Tyr Lys Glu Gly Tyr Gly Glu Gly Cys Val Thr Ile
1025                1030                1035                1040
His Glu Ile Glu Asn Asn Thr Asp Glu Leu Lys Phe Ser Asn Cys Val
                1045                1050                1055
Glu Glu Glu Val Tyr Pro Asn Asn Thr Val Thr Cys Asn Asp Tyr Thr
            1060                1065                1070
Ala Asn Gln Glu Glu Tyr Gly Gly Ala Tyr Thr Ser Arg Asn Arg Gly
            1075                1080                1085
Tyr Asp Glu Thr Tyr Gly Ser Asn Ser Ser Val Pro Ala Asp Tyr Ala
        1090                1095                1100
Ser Val Tyr Glu Glu Lys Ser Tyr Thr Asp Gly Arg Arg Asp Asn Pro
1105                1110                1115                1120
Cys Glu Ser Asn Arg Gly Tyr Gly Asp Tyr Thr Pro Leu Pro Ala Gly
                1125                1130                1135
Tyr Val Thr Lys Glu Leu Glu Tyr Phe Pro Glu Thr Asp Lys Val Trp
            1140                1145                1150
Ile Glu Ile Gly Glu Thr Glu Gly Thr Phe Ile Val Asp Ser Val Glu
```

Leu Leu Leu Met Glu Glu
    1170

<210> SEQ ID NO 7
<211> LENGTH: 1815
<212> TYPE: DNA
<213> ORGANISM: Artificial Sequence
<220> FEATURE:
<223> OTHER INFORMATION: Synthetic B.t. toxin gene

<400> SEQUENCE: 7

| | | | | | |
|---|---|---|---|---|---|
| atggagaaca | acatacagaa | tcagtgtgtc | ccctacaact | gcctcaacaa | tcctgaagta | 60 |
| gagattctca | cgaagaaag | gtcgactggc | agattgccgt | tagacatctc | cctgtcccctt | 120 |
| acacgattcc | tgttgtctga | gttcgttcct | ggtgtgggtg | ttgcgtttgg | cctcttcgat | 180 |
| ctcatctggg | ggttcatcac | tccatctgat | tggagcctct | tcttctaca | gattgaacag | 240 |
| ttgattgaac | aaaggattga | gaccttagaa | aggaatcggg | ccatcactac | acttcgtggg | 300 |
| ttagcagaca | gctatgagat | ctacattgaa | gcactaagag | agtgggaagc | caatcctaac | 360 |
| aatgcacaac | tgagagaaga | tgtgcgcata | cgctttgcta | acacagatga | tgctttgatc | 420 |
| acagccatca | caacttcac | acttaccagc | ttcgagattc | tcttctctc | ggtctatgtt | 480 |
| caagctgcta | accttcactt | gtcactactg | agggatgctg | tgtcgtttgg | ccaaggttgg | 540 |
| ggactggaca | tagctactgt | caacaatcac | tacaacagac | tcatcaatct | gattcatcga | 600 |
| tacacgaaac | attgtttgga | tacctacaat | cagggattgg | agaatctgag | aggtactaac | 660 |
| actcgtcaat | gggctaggtt | caatcagttc | aggagagacc | ttacacttac | tgtgttagac | 720 |
| atagttgctc | tctttccgaa | ctatgatgtt | cgtacctatc | cgattcaaac | gtcatcccaa | 780 |
| cttacaaggg | agatctacac | cagttcagtc | attgaagact | ctccagtttc | tgcgaacata | 840 |
| ccgaatggtt | tcaacagggc | tgagtttgga | gtcagacctc | cccatctcat | ggacttcatg | 900 |
| aactctttgt | ttgtgactgc | agaaactgtt | agatcgcaaa | ctgtgtgggg | aggacactta | 960 |
| gttagctcaa | ggaacacggc | tggcaatcgt | atcaactttc | ctagttacgg | ggtcttcaat | 1020 |
| cccgggggtg | ccatctggat | tgcagatgaa | gatccacgtc | cttctatcg | gaccttgtca | 1080 |
| gatcctgtct | tcgttcgagg | aggctttggc | aatcctcact | atgtactagg | tcttagggga | 1140 |
| gtggcctttc | aacaaactgg | tacgaatcac | acacgcacat | tcaggaactc | cgggaccatt | 1200 |
| gactctctag | atgagatacc | acctcaagac | aacagcggcg | caccttggaa | tgactactcg | 1260 |
| catgtgctga | atcatgttac | ctttgtgcgc | tggccaggtg | agatctctgg | ttccgactca | 1320 |
| tggagagcac | ctatgttctc | ttggacgcat | cgtagcgcta | cacctacaaa | caccattgat | 1380 |
| ccagaaagaa | tcactcagat | tcccttggtg | aaggcacaca | cacttcagtc | aggaactaca | 1440 |
| gttgtaagag | ggccggggtt | cacgggagga | gacattcttc | gaaggactag | tggaggacca | 1500 |
| ttcgcgtaca | ccattgtcaa | catcaatggg | caacttcccc | aaaggtatcg | tgctaggata | 1560 |
| cgctatgcct | ctactaccaa | tctacgaatc | tatgttacgg | ttgcaggtga | acggatcttt | 1620 |
| gctggtcagt | tcaacaagac | aatggatacc | ggtgatccac | ttacattcca | atctttctcc | 1680 |
| tacgccacta | tcaacaccgc | gttcaccttt | ccaatgagcc | agagcagttt | cacagtaggt | 1740 |
| gctgataccct | tcagttcagg | gaacgaagtg | tacattgata | ggtttgagtt | gattccagtt | 1800 |
| actgctacac | tcgag | | | | | 1815 |

<210> SEQ ID NO 8

<211> LENGTH: 1815
<212> TYPE: DNA
<213> ORGANISM: Artificial Sequence
<220> FEATURE:
<223> OTHER INFORMATION: Synthetic B.t. toxin gene

<400> SEQUENCE: 8

| | | | | | |
|---|---|---|---|---|---|
| atggagaaca | acatacagaa | tcagtgcgtc | ccctacaact | gcctcaacaa | tcctgaggta | 60 |
| gagattctca | acgaagagag | gtcgacgggc | agactgccgc | tggacatctc | cctgtccctc | 120 |
| acacgctttc | tcctgtctga | gttcgttcca | gtgtgggag | tcgcgtttgg | cctgttcgac | 180 |
| ctcatctggg | gcttcatcac | tccgtcggat | ggagcctct | tcttctcca | gatcgagcag | 240 |
| ttgattgaac | agaggattga | gaccttggag | aggaaccggg | ccatcactac | ccttcgtggc | 300 |
| ttagcagaca | gctacgagat | ctacattgaa | gccctacggg | agtgggaggc | caatcccaac | 360 |
| aatgcccaac | tgcgggaaga | tgtgcgtatc | cgcttcgcga | acaccgatga | cgctctgatc | 420 |
| accgccatca | caacttcac | ccttaccagc | ttcgagatac | ctctcctctc | ggtctatgtt | 480 |
| caagctgcga | acctgcactt | gtcactactg | cgcgacgctg | tgtcgtttgg | gcaagggtgg | 540 |
| ggcctggaca | tcgctacggt | caacaaccac | tacaaccgcc | tcatcaatct | gattcatcga | 600 |
| tacacgaaac | actgtctgga | tacctacaat | cagggcttgg | agaacctgag | aggtacgaac | 660 |
| actcgccagt | gggccaggtt | caaccagttc | aggcgcgacc | ttacacttac | tgtgctggac | 720 |
| atagtcgctc | tctttccgaa | ctacgacgtt | cgtacctatc | cgatccaaac | gagttcccag | 780 |
| cttaccaggg | agatctacac | cagctccgtc | attgaagact | ctccagtgtc | ggcgaacata | 840 |
| cccaatggct | tcaacagggc | tgagttcgga | gtccgcccac | cccatctcat | ggacttcatg | 900 |
| aactctctgt | tcgtgactgc | agagactgtt | agatcccaaa | cggtgtgggg | aggccactta | 960 |
| gtcagctcac | gcaacacggc | gggcaatcgg | atcaactttc | ctagctacgg | ggtgttcaat | 1020 |
| cccgggggcg | ccatctggat | tgcagatgaa | gatccgcggc | ccttctatcg | gaccttgtcc | 1080 |
| gatcctgtct | tcgtccgagg | aggctttggc | aaccctcact | acgtactcgg | tctcaggggc | 1140 |
| gtggccttcc | aacagactgg | tacgaatcac | acccgcacat | tcaggaactc | cggaccatc | 1200 |
| gactctctag | acgagatccc | gcctcaagac | aacagcggcg | caccttggaa | tgactactcc | 1260 |
| cacgtgctga | atcatgttac | ctttgtgcgc | tggccaggtg | agatctcagg | ctccgactca | 1320 |
| tggcgcgcac | caatgttctc | gtggacgcat | cgtagcgcta | cccccacaaa | caccattgat | 1380 |
| ccggagagaa | tcactcagat | tcccttggtg | aaggcccaca | cacttcagtc | aggcacgaca | 1440 |
| gtggtcagag | ggccggggtt | cacgggagga | gacatccttc | gacgcactag | tggcggacca | 1500 |
| ttcgcgtaca | ccattgtcaa | catcaacggg | cagcttcccc | aaaggtatcg | tgccaggata | 1560 |
| cgctatgcct | ctactaccaa | tctacgcatc | tacgttacgg | tggcaggcga | gcggatcttc | 1620 |
| gcgggtcagt | tcaacaagac | catggacacc | ggtgatccac | tcacattcca | gtctttctcc | 1680 |
| tacgccacga | tcaacaccgc | gttcaccttt | ccgatgagcc | agagcagctt | cacagtaggt | 1740 |
| gctgatacct | tcagttccgg | caacgaagtg | tacattgaca | ggtttgagtt | gatcccagtt | 1800 |
| actgccacac | tcgag | | | | | 1815 |

<210> SEQ ID NO 9
<211> LENGTH: 1641
<212> TYPE: DNA
<213> ORGANISM: Artificial Sequence
<220> FEATURE:
<223> OTHER INFORMATION: Synthetic B.t. protoxin gene

<400> SEQUENCE: 9

```
gcaacactcg aggcagagtc tgacttggaa agagcacaga aggcggtgaa tgctctgttc    60
acttcgtcca atcagattgg gctcaagaca gatgtgactg actatcacat cgatcgcgtt   120
tccaaccttg ttgagtgcct ctctgatgag ttctgtttgg atgagaagaa ggagttgtcc   180
gagaaggtca acatgctaa gcgacttagt gatgagcgga acttgcttca agatcccaac    240
tttcgcggga tcaacaggca actagatcgt ggatggaggg gaagtacgga catcaccatt   300
caaggaggtg atgatgtgtt caaggagaac tatgttacgc tcttgggtac ctttgatgag   360
tgctatccaa catcctgta ccagaagata gatgaatcga aactcaaagc ctacacaaga    420
taccagttga gaggttacat cgaggacagt caagaccttg agatctacct catcagatac   480
aacgccaaac atgagacagt caatgtgcct gggacgggtt cactctggcc actttcagcc   540
ccaagtccca tcggcaagtg tgcccatcac tcacaccact ctccttgga catagacgtt    600 ggctgtaccg acctgaacga agacctcggt gtgtgggtga tcttcaagat caagactcaa   660
gatggccatg ccaggctagg caatctggag tttctagaag agaaaccact tgttggagaa   720
gccctcgcta gagtgaagag ggctgagaag aagtggaggg acaagagaga gaagttggaa   780
tgggaaacaa acattgtgta caaagaagcc aaagaaagcg ttgacgctct gtttgtgaac   840
tctcagtatg ataggctcca agctgatacc aacatagcta tgattcatgc tgcagacaaa   900
cgcgttcata gcattcggga agcttacctt cctgaactta gcgtgattcc gggtgtcaat   960
gctgctatct ttgaagagtt agaagggcgc atcttcactg cattctcctt gtatgatgcg  1020
aggaatgtca tcaagaatgg tgacttcaac aatggcctat cctgctggaa tgtgaaaggg  1080
cacgtagatg tagaagaaca gaacaatcac cgctctgtcc ttgttgttcc tgagtgggaa  1140
gcagaagttt cacaagaagt tcgtgtctgt cctggtcgtg gctacattct tcgtgttacc  1200
gcgtacaaag aaggatacgg agaaggttgc gtcaccatac acgagattga gaacaacacc  1260
gacgagctga agttcagcaa ctgcgtcgag gaggaagtct acccaaacaa caccgtaact  1320
tgcaatgact acactgcgac tcaagaggag tatgagggta cttacacttc tcgcaatcga  1380
ggatacgatg gagcctatga gagcaactct tctgtacccg ctgactatgc atcagcctat  1440
gaggagaagg cttacaccga tggacgtagg gacaatcctt gcgaatctaa cagaggctat  1500
ggggactaca caccgttacc agccggctat gtcaccaaag agttagagta cttttccagaa 1560 accgacaagg tttggattga gattggagaa acggaaggaa cattcattgt tgatagcgtg  1620
gagttacttc tgatggagga a                                             1641
```

<210> SEQ ID NO 10
<211> LENGTH: 1635
<212> TYPE: DNA
<213> ORGANISM: Artificial Sequence
<220> FEATURE:
<223> OTHER INFORMATION: Synthetic B.t. protoxin gene

<400> SEQUENCE: 10

```
ctcgaggctg agagcgatct agagagggct cagaaggctg tgaacgctct cttcaccagc    60
agcaaccaga tcggtctcaa gaccgatgtt accgactacc acatcgatag ggttagcaat   120
cttgtggagt gtcttagcga cgagttctgc cttgacgaga gaaagagct agcgagaag    180 gtgaagcacg ctaagaggct tagcgatgag aggaaccttc tccaagaccc taacttcagg   240
ggtatcaaca gacagcttga taggggttgg agggggtagca ccgacatcac tatccaaggt   300
ggtgacgacg tgttcaaaga gaactacgtt acccttcttg gtactttcga cgaatgctac   360
```

```
cctacctacc tctatcagaa gatcgatgag agcaagctca aggcttacac caggtatcaa    420
cttaggggat acattgagga tagccaggat ctggagatct atctcatccg ttacaatgct    480
aagcacgaga ccgtgaacgt tcctggaacc ggtagccttt ggcctcttag tgcacctagc    540
cctatcggta agtgcgctca ccacagccac cacttcagcc ttgacatcga tgttggttgc    600
accgatctca acgaggatct tggtgtttgg gtcatcttca agatcaagac ccaagatggt    660
cacgctaggc ttggaaacct tgagttcctt gaggagaagc ctcttgttgg tgaggctctt    720
gctagggtga agagagcaga gaagaagtgg agagacaaga gggagaagct tgagtgggag    780
accaacatcg tgtacaagga ggctaaggag agcgttgatg ctctcttcgt gaacagccag    840
tacgataggc ttcaagcaga cactaacatc gctatgatcc acgctgctga caagagggtt    900
cacagcatca gggaggcata ccttccagag cttagcgtga tccctggagt gaacgcagca    960
atcttcgagg agcttgaggg taggatcttc accgctttca gcctctacga tgctaggaac   1020
gtgatcaaga acggagactt caacaacggt cttagctgct ggaacgtgaa gggtcacgtt   1080
gatgttgagg agcagaacaa ccacaggagc gttctcgtgg tgccagagtg ggaggctgaa   1140
gttagccaag aggttagggt ttgccctggt aggggttaca tccttagggt gactgcttac   1200
aaggagggtt acggtgaggg ttgcgttacc atccacgaga tcgagaacaa cactgatgag   1260
ctcaagttca gtaactgtgt ggaggaggag gtgtacccta caacactgt tacctgcaac    1320 gactacaccg ctacccagga agagtacgag ggaacctaca ccagcaggaa cagggggttac   1380 gatggtgctt acgagagcaa cagcagcgtt cctgctgact acgctagcgc atacgaagag   1440
aaagcataca ctgatggtag gagggacaac ccttgcgaga gcaacagggg ttacggtgac   1500 tacaccccctc ttcctgctgg ttacgttacc aaggagcttg agtacttccc tgagactgac   1560
aaagtgtgga tcgagatcgg tgagaccgag ggaaccttca tcgtggacag cgttgagctt   1620
cttctcatgg aggag                                                    1635
```

<210> SEQ ID NO 11
<211> LENGTH: 547
<212> TYPE: PRT
<213> ORGANISM: Artificial Sequence
<220> FEATURE:
<223> OTHER INFORMATION: Toxin encoded by synthetic B.t. gene

<400> SEQUENCE: 11

```
Ala Thr Leu Glu Ala Glu Ser Asp Leu Glu Arg Ala Gln Lys Ala Val
  1               5                  10                  15

Asn Ala Leu Phe Thr Ser Ser Asn Gln Ile Gly Leu Lys Thr Asp Val
             20                  25                  30

Thr Asp Tyr His Ile Asp Arg Val Ser Asn Leu Val Glu Cys Leu Ser
         35                  40                  45

Asp Glu Phe Cys Leu Asp Glu Lys Lys Glu Leu Ser Glu Lys Val Lys
     50                  55                  60

His Ala Lys Arg Leu Ser Asp Glu Arg Asn Leu Leu Gln Asp Pro Asn
 65                  70                  75                  80

Phe Arg Gly Ile Asn Arg Gln Leu Asp Arg Gly Trp Arg Gly Ser Thr
                 85                  90                  95

Asp Ile Thr Ile Gln Gly Gly Asp Asp Val Phe Lys Glu Asn Tyr Val
            100                 105                 110

Thr Leu Leu Gly Thr Phe Asp Glu Cys Tyr Pro Thr Tyr Leu Tyr Gln
        115                 120                 125

Lys Ile Asp Glu Ser Lys Leu Lys Ala Tyr Thr Arg Tyr Gln Leu Arg
```

```
            130                 135                 140
Gly Tyr Ile Glu Asp Ser Gln Asp Leu Glu Ile Tyr Leu Ile Arg Tyr
145                 150                 155                 160
Asn Ala Lys His Glu Thr Val Asn Val Pro Gly Thr Gly Ser Leu Trp
                165                 170                 175
Pro Leu Ser Ala Pro Ser Pro Ile Gly Lys Cys Ala His His Ser His
                180                 185                 190
His Phe Ser Leu Asp Ile Asp Val Gly Cys Thr Asp Leu Asn Glu Asp
                195                 200                 205
Leu Gly Val Trp Val Ile Phe Lys Ile Lys Thr Gln Asp Gly His Ala
                210                 215                 220
Arg Leu Gly Asn Leu Glu Phe Leu Glu Glu Lys Pro Leu Val Gly Glu
225                 230                 235                 240
Ala Leu Ala Arg Val Lys Arg Ala Glu Lys Lys Trp Arg Asp Lys Arg
                245                 250                 255
Glu Lys Leu Glu Trp Glu Thr Asn Ile Val Tyr Lys Glu Ala Lys Glu
                260                 265                 270
Ser Val Asp Ala Leu Phe Val Asn Ser Gln Tyr Asp Arg Leu Gln Ala
                275                 280                 285
Asp Thr Asn Ile Ala Met Ile His Ala Ala Asp Lys Arg Val His Ser
                290                 295                 300
Ile Arg Glu Ala Tyr Leu Pro Glu Leu Ser Val Ile Pro Gly Val Asn
305                 310                 315                 320
Ala Ala Ile Phe Glu Glu Leu Glu Gly Arg Ile Phe Thr Ala Phe Ser
                325                 330                 335
Leu Tyr Asp Ala Arg Asn Val Ile Lys Asn Gly Asp Phe Asn Asn Gly
                340                 345                 350
Leu Ser Cys Trp Asn Val Lys Gly His Val Asp Val Glu Glu Gln Asn
                355                 360                 365
Asn His Arg Ser Val Leu Val Val Pro Glu Trp Glu Ala Glu Val Ser
                370                 375                 380
Gln Glu Val Arg Val Cys Pro Gly Arg Gly Tyr Ile Leu Arg Val Thr
385                 390                 395                 400
Ala Tyr Lys Glu Gly Tyr Gly Glu Gly Cys Val Thr Ile His Glu Ile
                405                 410                 415
Glu Asn Asn Thr Asp Glu Leu Lys Phe Ser Asn Cys Val Glu Glu Glu
                420                 425                 430
Val Tyr Pro Asn Asn Thr Val Thr Cys Asn Asp Tyr Thr Ala Thr Gln
                435                 440                 445
Glu Glu Tyr Glu Gly Thr Tyr Thr Ser Arg Asn Arg Gly Tyr Asp Gly
                450                 455                 460
Ala Tyr Glu Ser Asn Ser Ser Val Pro Ala Asp Tyr Ala Ser Ala Tyr
465                 470                 475                 480
Glu Glu Lys Ala Tyr Thr Asp Gly Arg Arg Asp Asn Pro Cys Glu Ser
                485                 490                 495
Asn Arg Gly Tyr Gly Asp Tyr Thr Pro Leu Pro Ala Gly Tyr Val Thr
                500                 505                 510
Lys Glu Leu Glu Tyr Phe Pro Glu Thr Asp Lys Val Trp Ile Glu Ile
                515                 520                 525
Gly Glu Thr Glu Gly Thr Phe Ile Val Asp Ser Val Glu Leu Leu Leu
                530                 535                 540
Met Glu Glu
545
```

<210> SEQ ID NO 12
<211> LENGTH: 3468
<212> TYPE: DNA
<213> ORGANISM: Artificial Sequence
<220> FEATURE:
<223> OTHER INFORMATION: Synthetic B.t. toxin gene

<400> SEQUENCE: 12

| | | | | | |
|---|---|---|---|---|---|
| atggacaaca | atcccaacat | caacgagtgc | attccttaca | actgcctgag | caaccctgag | 60 |
| gttgaggtgc | tgggtggaga | acggattgag | actggttaca | cacctatcga | catctcgttg | 120 |
| tcacttaccc | aattcctttt | gtcagagttc | gtgcccggtg | ctggattcgt | gcttggactt | 180 |
| gtcgatatca | tttggggaat | ctttggtccc | tctcaatggg | acgcctttct | tgtacagata | 240 |
| gagcaactta | tcaaccaaag | gattgaagag | ttcgctagga | accaagccat | ctcaaggtta | 300 |
| gaaggcctca | gcaaccttta | ccagatttac | gcagaatctt | tcgagagtg | ggaagcagac | 360 |
| ccgaccaatc | ctgccttaag | agaggagatg | cgcattcaat | tcaatgacat | gaacagcgcg | 420 |
| ctgacgaccg | caattccgct | cttcgccgtt | cagaattacc | aagttcctct | tttatccgtg | 480 |
| tacgtgcagg | ctgccaacct | gcacttgtcg | gtgctccgcg | atgtctccgt | gttcggacaa | 540 |
| cggtggggct | tgatgccgc | aactatcaat | agtcgttata | atgatctgac | taggcttatt | 600 |
| ggcaactata | ccgattatgc | tgttcgctgg | tacaacacgg | tctcgaacg | tgtctgggga | 660 |
| ccggattcta | gagattgggt | caggtacaac | cagttcaggc | gagagttgac | actaactgtc | 720 |
| ctagacattg | tcgctctctt | tcccaactac | gactctaggc | gctacccaat | ccgtactgtg | 780 |
| tcacaattga | cccgggaaat | ctacacaaac | ccagtcctcg | agaacttcga | cggtagcttt | 840 |
| cgaggctcgg | ctcagggcat | agagagaagc | atcaggtctc | cacacctgat | ggacatattg | 900 |
| aacagtatca | cgatctacac | cgatgcgcac | cgcggttatt | actactggtc | agggcatcag | 960 |
| atcatggcat | cacccgttgg | gttctctgga | ccagaattca | ctttcccact | ttacgggact | 1020 |
| atgggcaatg | cagctccaca | acaacgtatt | gttgctcaac | tcggtcaggg | cgtgtataga | 1080 |
| accttgtcca | gcactctata | taggagacct | ttcaacatcg | gcatcaacaa | tcaacaattg | 1140 |
| tctgtgcttg | acgggacaga | atttgcctat | ggaacctcct | caaatctgcc | atccgctgtc | 1200 |
| tacagaaaga | gcggaacagt | tgatagcttg | gatgagatcc | ctccacagaa | caacaacgtt | 1260 |
| ccacctaggc | aagggtttag | ccatcgcctt | agccatgtgt | ccatgttccg | ttcaggcttt | 1320 |
| agtaatagca | gcgttagtat | catcagagct | ccgatgttct | cttggataca | tcgtagtgct | 1380 |
| gagtttaaca | acataattgc | atccgatagc | attactcaga | tcccagctgt | caaggggaac | 1440 |
| tttctcttta | atggttctgt | catttcagga | ccaggattca | ctggaggcga | cttggttagg | 1500 |
| ctgaattctt | ccggcaacaa | catccagaat | agagggtata | ttgaagtgcc | cattcacttc | 1560 |
| ccatcgacat | ctaccagata | tcgtgttcgt | gtaaggtatg | cctctgttac | ccctattcac | 1620 |
| ctcaacgtca | attggggtaa | ttcctccatc | ttttccaata | cagtaccagc | gacagctaca | 1680 |
| tccttggata | atctccaatc | tagcgatttc | ggttacttcg | aaagtgccaa | tgccttcacc | 1740 |
| tcttccctag | gtaacatagt | aggtgttaga | aatttctccg | gaaccgccgg | agtgataatc | 1800 |
| gaccgcttcg | aattcattcc | cgttactgca | acgctcgagg | cagaatctga | tttagaaaga | 1860 |
| gcacaaaagg | cggtgaatgc | cctgtttact | tcttccaatc | aaatcgggtt | aaaaaccgat | 1920 |
| gtgacggatt | atcatatcga | tcgagtatcc | aatttagttg | agtgtttatc | tgatgaattt | 1980 |
| tgtctggatg | aaaaaaaaga | attgtccgag | aaagtcaaac | atgcgaagcg | acttagtgat | 2040 |

-continued

```
gagcggaatt tacttcaaga tccaaacttt agagggatca atagacaact agaccgtggc    2100
tggagaggaa gtacggatat taccatccaa ggaggcgatg acgtattcaa agagaattac    2160
gttacgctat tgggtaccrt tgatgagtgc tatccaacgt atttatatca aaaatagat    2220
gagtcgaaat taaaagccta tacccgttac caattaagag ggtatatcga agatagtcaa    2280
gacttagaaa tctatttaat tcgctacaat gccaaacacg aaacagtaaa tgtgccaggt    2340
acgggttcct tatggccgct ttcagcccca agtccaatcg gaaaatgtgc ccatcattcc    2400
catcatttct ccttggacat tgatgttgga tgtacagact aaatgagga cttaggtgta    2460
tgggtgatat tcaagattaa gacgcaagat ggccatgcaa gactaggaaa tctagaattt    2520
ctcgaagaga aaccattagt aggagaagca ctagctcgtg tgaaaagagc ggagaaaaaa    2580
tggagagaca aacgtgaaaa attggaatgg gaaacaaata ttgtttataa agaggcaaaa    2640
gaatctgtag atgctttatt tgtaaactct caatatgata gattacaagc ggataccaac    2700
atcgcgatga ttcatgcggc agataaacgc gttcatagca ttcgagaagc ttatctgcct    2760
gagctgtctg tgattccggg tgtcaatgcg gctattttg aagaattaga agggcgtatt    2820
ttcactgcat tctccctata tgatgcgaga aatgtcatta aaaatggtga ttttaataat    2880
ggcttatcct gctggaacgt gaaagggcat gtagatgtag aagaacaaaa caaccaccgt    2940
tcggtccttg ttgttccgga atgggaagca gaagtgtcac aagaagttcg tgtctgtccg    3000
ggtcgtggct atatccttcg tgtcacagcg tacaaggagg gatatggaga aggttgcgta    3060
accattcatg agatcgagaa caatacagac gaactgaagt ttagcaactg tgtagaagag    3120
gaagtatatc caaacaacac ggtaacgtgt aatgattata ctgcgactca agaagaatat    3180
gagggtacgt acacttctcg taatcgagga tatgacggag cctatgaaag caattcttct    3240
gtaccagctg attatgcatc agcctatgaa gaaaaagcat atacagatgg acgaagagac    3300
aatccttgtg aatctaacag aggatatggg gattacacac cactaccagc tggctatgtg    3360
acaaaagaat tagagtactt cccagaaacc gataaggtat ggattgagat cggagaaacg    3420
gaaggaacat tcatcgtgga cagcgtggaa ttacttctta tggaggaa                 3468
```

<210> SEQ ID NO 13
<211> LENGTH: 3468
<212> TYPE: DNA
<213> ORGANISM: Artificial Sequence
<220> FEATURE:
<223> OTHER INFORMATION: Synthetic B.t. toxin gene

<400> SEQUENCE: 13

```
atggacaaca atcccaacat caacgagtgc attccttaca actgcctgag caaccctgag     60
gttgaggtgc tgggtggaga acggattgag actggttaca cacctatcga catctcgttg    120
tcacttaccc aattccttt gtcagagttc gtgcccggtg ctggattcgt gcttggactt    180
gtcgatatca tttggggaat cttggtccc tctcaatggg acgcctttct tgtacagata    240
gagcaactta tcaaccaaag gattgaagag ttcgctagga accaagccat ctcaaggtta    300
gaaggcctca gcaacctta ccagatttac gcagaatctt ttcgagagtg gaagcagac    360
ccgaccaatc ctgccttaag agaggagatg cgcattcaat tcaatgacat gaacagcgcg    420
ctgacgaccg caattccgct cttcgccgtt cagaattacc aagttcctct tttatccgtg    480
tacgtgcagg ctgccaacct gcacttgtcg gtgctccgcg atgtctccgt gttcggacaa    540
cggtggggct tgatgccgc aactatcaat agtcgttata atgatctgac taggcttatt    600
ggcaactata ccgattatgc tgttcgctgg tacaacacgg gtctcgaacg tgtctgggga    660
```

```
ccggattcta gagattgggt caggtacaac cagttcaggc gagagttgac actaactgtc      720
ctagacattg tcgctctctt tcccaactac gactctaggc gctacccaat ccgtactgtg      780
tcacaattga cccgggaaat ctacacaaac ccagtcctcg agaacttcga cggtagcttt      840
cgaggctcgg ctcagggcat agagagaagc atcaggtctc cacacctgat ggacatattg      900
aacagtatca cgatctacac cgatgcgcac cgcggttatt actactggtc agggcatcag      960
atcatggcat cacccgttgg gttctctgga ccagaattca ctttcccact ttacgggact     1020
atgggcaatg cagctccaca acaacgtatt gttgctcaac tcggtcaggg cgtgtataga     1080
accttgtcca gcactctata taggagacct ttcaacatcg gcatcaacaa tcaacaattg     1140
tctgtgcttg acgggacaga atttgcctat ggaacctcct caaatctgcc atccgctgtc     1200
tacagaaaga gcggaacagt tgatagcttg gatgagatcc ctccacagaa caacaacgtt     1260
ccacctaggc aagggtttag ccatcgcctt agccatgtgt ccatgttccg ttcaggcttt     1320
agtaatagca gcgttagtat catcagagct ccgatgttct cttggataca tcgtagtgct     1380
gagtttaaca acataattgc atccgatagc attactcaga tcccagctgt caggggaac      1440 tttctctttta atggttctgt catttcagga ccaggattca ctggaggcga cttggttagg     1500
ctgaattctt ccggcaacaa catccagaat agagggtata ttgaagtgcc cattcacttc     1560
ccatcgacat ctaccagata tcgtgttcgt gtaaggtatg cctctgttac ccctattcac     1620
ctcaacgtca attggggtaa ttcctccatc ttttccaata cagtaccagc gacagctaca     1680
tccttggata atctccaatc tagcgatttc ggttacttcg aaagtgccaa tgccttcacc     1740
tcttccctag gtaacatagt aggtgttaga aatttctccg gaaccgccgg agtgataatc     1800
gaccgcttcg aattcattcc cgttactgca acgctcgagg cagagtctga cttggaaaga     1860
gcacagaagg cggtgaatgc tctgttcact tcgtccaatc agattgggct caagacagat     1920
gtgactgact atcacatcga tcgcgtttcc aaccttgttg agtgcctctc tgatgagttc     1980
tgtttggatg agaagaagga gttgtccgag aaggtcaaac atgctaagcg acttagtgat     2040
gagcggaact tgcttcaaga tcccaacttt cgcgggatca acaggcaact agatcgtgga     2100 tggagggaa gtacggacat caccattcaa ggaggtgatg atgtgttcaa ggagaactat     2160
gttacgctct tgggtacctt tgatgagtgc tatccaacat acctgtacca gaagatagat     2220
gaatcgaaac tcaaagccta cacaagatac cagttgagag gttacatcga ggacagtcaa     2280
gaccttgaga tctacctcat cagatacaac gccaaacatg agacagtcaa tgtgcctggg     2340
acgggttcac tctggccact ttcagcccca agtcccatcg gcaagtgtgc ccatcactca     2400
caccacttct ccttggacat agacgttggc tgtaccgacc tgaacgaaga cctcggtgtg     2460
tgggtgatct tcaagatcaa gactcaagat ggccatgcca ggctaggcaa tctggagttt     2520
ctagaagaga accacttgt tggagaagcc ctcgctagtg tgaagagggc tgagaagaag     2580
tggagggaca agagagagaa gttggaatgg gaaacaaaca ttgtgtacaa agaagccaaa     2640
gaaagcgttg acgctctgtt tgtgaactct cagtatgata ggctccaagc tgataccaac     2700
atagctatga ttcatgctgc agacaaacgc gttcatagca ttcgggaagc ttaccttcct     2760
gaacttagcg tgattccggg tgtcaatgct gctatctttg aagagttaga agggcgcatc     2820
ttcactgcat tctccttgta tgatgcgagg aatgtcatca agaatggtga cttcaacaat     2880
ggcctatcct gctggaatgt gaaagggcac gtagatgtag aagaacagaa caatcaccgc     2940
tctgtccttg ttgttcctga gtgggaagca gaagtttcac aagaagttcg tgtctgtcct     3000
```

| | |
|---|---|
| ggtcgtggct acattcttcg tgttaccgcg tacaaagaag gatacggaga aggttgcgtc | 3060 |
| accatacacg agattgagaa caacaccgac gagctgaagt tcagcaactg cgtcgaggag | 3120 |
| gaagtctacc caaacaacac cgtaacttgc aatgactaca ctgcgactca agaggagtat | 3180 |
| gagggtactt acacttctcg caatcgagga tacgatggag cctatgagag caactcttct | 3240 |
| gtacccgctg actatgcatc agcctatgag gagaaggctt acaccgatgg acgtagggac | 3300 |
| aatccttgcg aatctaacag aggctatggg gactacacac cgttaccagc cggctatgtc | 3360 |
| accaaagagt tagagtactt tccagaaacc gacaaggttt ggattgagat tggagaaacg | 3420 |
| gaaggaacat tcattgttga tagcgtggag ttacttctga tggaggaa | 3468 |

<210> SEQ ID NO 14
<211> LENGTH: 3468
<212> TYPE: DNA
<213> ORGANISM: Artificial Sequence
<220> FEATURE:
<223> OTHER INFORMATION: Synthetic B.t. toxin gene

<400> SEQUENCE: 14

| | |
|---|---|
| atggacaaca atcccaacat caacgagtgc attccttaca actgcctgag caaccctgag | 60 |
| gttgaggtgc tgggtggaga acggattgag actggttaca cacctatcga catctcgttg | 120 |
| tcacttaccc aattcctttt gtcagagttc gtgcccggtg ctggattcgt gcttggactt | 180 |
| gtcgatatca tttggggaat ctttggtccc tctcaatggg acgcctttct tgtacagata | 240 |
| gagcagttaa ttaaccaaag aatagaagaa ttcgctagga accaagccat ctcaaggtta | 300 |
| gaaggcctca gcaaccttta ccagatttac gcagaatctt tcgagagtg ggaagcagac | 360 |
| ccgaccaatc ctgccttaag agaggagatg cgcattcaat tcaatgacat gaacagcgcg | 420 |
| ctgacgaccg caattccgct cttcgccgtt cagaattacc aagttcctct tttatccgtg | 480 |
| tacgtgcagg ctgccaacct gcacttgtcg gtgctccgcg atgtctccgt gttcggacaa | 540 |
| cggtggggct tgatgccgc aactatcaat agtcgttata atgatctgac taggcttatt | 600 |
| ggcaactata ccgattatgc tgttcgctgg tacaacacgg tctcgaacg tgtctgggga | 660 |
| ccggattcta gagattgggt caggtacaac cagttcaggc gagagttgac actaactgtc | 720 |
| ctagacattg tcgctctctt tcccaactac gactctaggc gctacccaat ccgtactgtg | 780 |
| tcacaattga cccgggaaat ctacacaaac ccagtcctcg agaacttcga cggtagcttt | 840 |
| cgaggctcgg ctcagggcat agagagaagc atcaggtctc cacacctgat ggacatattg | 900 |
| aacagtatca cgatctacac cgatgcgcac cgcggttatt actactggtc agggcatcag | 960 |
| atcatggcat cacccgttgg gttctctgga ccagaattca ctttcccact ttacgggact | 1020 |
| atgggcaatg cagctccaca caacgtatt gttgctcaac tcggtcaggg cgtgtataga | 1080 |
| accttgtcca gcactctata taggagacct ttcaacatcg gcatcaacaa tcaacaattg | 1140 |
| tctgtgcttg acgggacaga atttgcctat ggaacctcct caaatctgcc atccgctgtc | 1200 |
| tacagaaaga gcggaacagt tgatagcttg gatgagatcc ctccacagaa caacaacgtt | 1260 |
| ccacctaggc aagggtttag ccatcgcctt agccatgtgt ccatgttccg ttcaggcttt | 1320 |
| agtaatagca gcgttagtat catcagagct ccgatgttct cttggataca tcgtagtgct | 1380 |
| gagtttaaca acataattgc atccgatagc attactcaga tcccagctgt caaggggaac | 1440 |
| tttctcttta tggttctgt catttcagga ccaggattca ctggaggcga cttggttagg | 1500 |
| ctgaattctt ccggcaacaa catccagaat agagggtata ttgaagtgcc cattcacttc | 1560 |
| ccatcgacat ctaccagata tcgtgttcgt gtaaggtatg cctctgttac ccctattcac | 1620 |

-continued

```
ctcaacgtca attggggtaa ttcctccatc ttttccaata cagtaccagc gacagctaca    1680
tccttggata tctccaatc tagcgatttc ggttacttcg aaagtgccaa tgccttcacc    1740
tcttccctag gtaacatagt aggtgttaga aatttctccg gaaccgccgg agtgataatc    1800
gaccgcttcg aattcattcc cgttactgca acgctcgagg cagagtctga cttggaaaga    1860
gcacagaagg cggtgaatgc tctgttcact tcgtccaatc agattgggct caagacagat    1920
gtgactgact atcacatcga tcgcgttttc aaccttgttg agtgcctctc tgatgagttc    1980
tgtttggatg agaagaagga gttgtccgag aaggtcaaac atgctaagcg acttagtgat    2040
gagcggaact tgcttcaaga tcccaacttt cgcgggatca acaggcaact agatcgtgga    2100 tggagggga gtacggacat caccattcaa ggaggtgatg atgtgttcaa ggagaactat    2160
gttacgctct tgggtacctt tgatgagtgc tatccaacat acctgtacca agagatagat    2220
gaatcgaaac tcaaagccta cacaagatac cagttgagag gttacatcga ggacagtcaa    2280
gaccttgaga tctacctcat cagatacaac gccaaacatg agacagtcaa tgtgcctggg    2340
acgggttcac tctggccact tcagccccca agtcccatcg gcaagtgtgc ccatcactca    2400
caccacttct ccttggacat agacgttggc tgtaccgacc tgaacgaaga cctcggtgtg    2460
tgggtgatct tcaagatcaa gactcaagat ggccatgcca ggctaggcaa tctggagttt    2520
ctagaagaga aaccacttgt tggagaagcc ctcgctagag tgaagagggc tgagaagaag    2580
tggagggaca agagagagaa gttggaatgg gaaacaaaca ttgtgtacaa agaagccaaa    2640
gaaagcgttg acgctctgtt tgtgaactct cagtatgata ggctccaagc tgataccaac    2700
atagctatga tcatgctgc agacaaacgc gttcatagca ttcgggaagc ttaccttcct    2760
gaacttagcg tgattccggg tgtcaatgct gctatctttg aagagttaga agggcgcatc    2820
ttcactgcat tctccttgta tgatgcgagg aatgtcatca gaatggtga cttcaacaat    2880 ggcctatcct gctggaatgt gaaagggcac gtagatgtag aagaacagaa caatcaccgc    2940
tctgtccttg ttgttcctga gtgggaagca gaagtttcac aagaagttcg tgtctgtcct    3000
ggtcgtggct acattcttcg tgttaccgcg tacaaagaag gatacggaga aggttgcgtc    3060
accatacacg agattgagaa caacaccgac gagctgaagt tcagcaactg cgtcgaggag    3120
gaagtctacc caaacaacac cgtaacttgc aatgactaca ctgcgactca agaggagtat    3180
gagggtactt acacttctcg caatcgagga tacgatggag cctatgagag caactcttct    3240 gtaccgctg actatgcatc agcctatgag gagaaggctt acaccgatgg acgtagggac    3300
aatccttgcg aatctaacag aggctatggg gactacacac cgttaccagc cggctatgtc    3360
accaaagagt tagagtactt tccagaaacc gacaaggttt ggattgagat tggagaaacg    3420
gaaggaacat tcattgttga tagcgtggag ttacttctga tggaggaa               3468
```

<210> SEQ ID NO 15
<211> LENGTH: 1156
<212> TYPE: PRT
<213> ORGANISM: Artificial Sequence
<220> FEATURE:
<223> OTHER INFORMATION: Toxin encoded by synthetic B.t. gene

<400> SEQUENCE: 15

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
             20                  25                  30
```

```
Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
```

-continued

```
            450                 455                 460
Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
                530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
                595                 600                 605

Thr Ala Thr Leu Glu Ala Glu Ser Asp Leu Glu Arg Ala Gln Lys Ala
                610                 615                 620

Val Asn Ala Leu Phe Thr Ser Ser Asn Gln Ile Gly Leu Lys Thr Asp
625                 630                 635                 640

Val Thr Asp Tyr His Ile Asp Arg Val Ser Asn Leu Val Glu Cys Leu
                645                 650                 655

Ser Asp Glu Phe Cys Leu Asp Glu Lys Lys Glu Leu Ser Glu Lys Val
                660                 665                 670

Lys His Ala Lys Arg Leu Ser Asp Glu Arg Asn Leu Leu Gln Asp Pro
                675                 680                 685

Asn Phe Arg Gly Ile Asn Arg Gln Leu Asp Arg Gly Trp Arg Gly Ser
690                 695                 700

Thr Asp Ile Thr Ile Gln Gly Gly Asp Asp Val Phe Lys Glu Asn Tyr
705                 710                 715                 720

Val Thr Leu Leu Gly Thr Phe Asp Glu Cys Tyr Pro Thr Tyr Leu Tyr
                725                 730                 735

Gln Lys Ile Asp Glu Ser Lys Leu Lys Ala Tyr Thr Arg Tyr Gln Leu
                740                 745                 750

Arg Gly Tyr Ile Glu Asp Ser Gln Asp Leu Glu Ile Tyr Leu Ile Arg
                755                 760                 765

Tyr Asn Ala Lys His Glu Thr Val Asn Val Pro Gly Thr Gly Ser Leu
770                 775                 780

Trp Pro Leu Ser Ala Pro Ser Pro Ile Gly Lys Cys Ala His His Ser
785                 790                 795                 800

His His Phe Ser Leu Asp Ile Asp Val Gly Cys Thr Asp Leu Asn Glu
                805                 810                 815

Asp Leu Gly Val Trp Val Ile Phe Lys Ile Lys Thr Gln Asp Gly His
                820                 825                 830

Ala Arg Leu Gly Asn Leu Glu Phe Leu Glu Glu Lys Pro Leu Val Gly
                835                 840                 845

Glu Ala Leu Ala Arg Val Lys Arg Ala Glu Lys Lys Trp Arg Asp Lys
                850                 855                 860

Arg Glu Lys Leu Glu Trp Glu Thr Asn Ile Val Tyr Lys Glu Ala Lys
865                 870                 875                 880
```

-continued

```
Glu Ser Val Asp Ala Leu Phe Val Asn Ser Gln Tyr Asp Arg Leu Gln
                885                 890                 895
Ala Asp Thr Asn Ile Ala Met Ile His Ala Ala Asp Lys Arg Val His
            900                 905                 910
Ser Ile Arg Glu Ala Tyr Leu Pro Glu Leu Ser Val Ile Pro Gly Val
        915                 920                 925
Asn Ala Ala Ile Phe Glu Glu Leu Glu Gly Arg Ile Phe Thr Ala Phe
    930                 935                 940
Ser Leu Tyr Asp Ala Arg Asn Val Ile Lys Asn Gly Asp Phe Asn Asn
945                 950                 955                 960
Gly Leu Ser Cys Trp Asn Val Lys Gly His Val Asp Val Glu Glu Gln
                965                 970                 975
Asn Asn His Arg Ser Val Leu Val Pro Glu Trp Glu Ala Glu Val
            980                 985                 990
Ser Gln Glu Val Arg Val Cys Pro Gly Arg Gly Tyr Ile Leu Arg Val
        995                 1000                1005
Thr Ala Tyr Lys Glu Gly Tyr Gly Glu Gly Cys Val Thr Ile His Glu
    1010                1015                1020
Ile Glu Asn Asn Thr Asp Glu Leu Lys Phe Ser Asn Cys Val Glu Glu
1025                1030                1035                1040
Glu Val Tyr Pro Asn Asn Thr Val Thr Cys Asn Asp Tyr Thr Ala Thr
                1045                1050                1055
Gln Glu Glu Tyr Glu Gly Thr Tyr Thr Ser Arg Asn Arg Gly Tyr Asp
            1060                1065                1070
Gly Ala Tyr Glu Ser Asn Ser Ser Val Pro Ala Asp Tyr Ala Ser Ala
        1075                1080                1085
Tyr Glu Glu Lys Ala Tyr Thr Asp Gly Arg Arg Asp Asn Pro Cys Glu
    1090                1095                1100
Ser Asn Arg Gly Tyr Gly Asp Tyr Thr Pro Leu Pro Ala Gly Tyr Val
1105                1110                1115                1120
Thr Lys Glu Leu Glu Tyr Phe Pro Glu Thr Asp Lys Val Trp Ile Glu
                1125                1130                1135
Ile Gly Glu Thr Glu Gly Thr Phe Ile Val Asp Ser Val Glu Leu Leu
            1140                1145                1150
Leu Met Glu Glu
        1155
```

<210> SEQ ID NO 16
<211> LENGTH: 1839
<212> TYPE: DNA
<213> ORGANISM: Artificial Sequence
<220> FEATURE:
<223> OTHER INFORMATION: Synthetic B.t. toxin gene

<400> SEQUENCE: 16

```
atggacaaca atcccaacat caacgagtgc attccttaca actgcctgag caaccctgag    60
gttgaggtgc tgggtggaga acggattgag actggttaca cacctatcga catctcgttg   120
tcacttaccc aattcctttt gtcagagttc gtgcccggtg ctggattcgt gcttggactt   180
gtcgatatca tttggggaat ctttggtccc tctcaatggg acgcctttct tgtacagata   240
gagcaactta tcaaccaaag gattgaagag ttcgctagga accaagccat ctcaaggtta   300
gaaggcctca gcaacctttta ccagatttac gcagaatctt ttcgagagtg ggaagcagac   360
ccgaccaatc ctgccttaag agaggagatg cgcattcaat tcaatgacat gaacagcgcg   420
```

-continued

```
ctgacgaccg caattccgct cttcgccgtt cagaattacc aagttcctct tttatccgtg      480
tacgtgcagg ctgccaacct gcacttgtcg gtgctccgcg atgtctccgt gttcggacaa      540 cggtgggget tgatgccgc aactatcaat agtcgttata atgatctgac taggcttatt      600
ggcaactata ccgattatgc tgttcgctgg tacaacacgg gtctcgaacg tgtctgggga      660
ccggattcta gagattggt caggtacaac cagttcaggc gagagttgac actaactgtc      720
ctagacattg tcgctctctt tcccaactac gactctaggc gctacccaat ccgtactgtg      780
tcacaattga cccgggaaat ctacacaaac ccagtcctcg agaacttcga cggtagcttt      840
cgaggctcgg ctcagggcat agagagaagc atcaggtctc cacacctgat ggacatattg      900
aacagtatca cgatctacac cgatgcgcac cgcggttatt actactggtc agggcatcag      960
atcatggcat cacccgttgg gttctctgga ccagaattca ctttcccact ttacgggact     1020
atgggcaatg cagctccaca caacgtatt gttgctcaac tcggtcaggg cgtgtataga     1080
accttgtcca gcactctata taggagacct ttcaacatcg gcatcaacaa tcaacaattg     1140
tctgtgcttg acgggacaga atttgcctat ggaacctcct caaatctgcc atccgctgtc     1200
tacagaaaga gcggaacagt tgatagcttg gatgagatcc ctccacagaa caacaacgtt     1260
ccacctaggc aagggtttag ccatcgcctt agccatgtgt ccatgttccg ttcaggcttt     1320
agtaatagca gcgttagtat catcagagct ccgatgttct cttggataca tcgtagtgct     1380
gagtttaaca acataattgc atccgatagc attactcaga tcccagctgt caaggggaac     1440 tttctctta atggttctgt catttcagga ccaggattca ctggaggcga cttggttagg     1500
ctgaattctt ccggcaacaa catccagaat agagggtata ttgaagtgcc cattcacttc     1560
ccatcgacat ctaccagata tcgtgttcgt gtaaggtatg cctctgttac ccctattcac     1620
ctcaacgtca attggggtaa ttcctccatc ttttccaata cagtaccagc gacagctaca     1680
tccttggata atctccaatc tagcgatttc ggttacttcg aaagtgccaa tgccttcacc     1740
tcttccctag gtaacatagt aggtgttaga aatttctccg gaaccgccgg agtgataatc     1800
gaccgcttcg aattcattcc cgttactgca acgctcgag                          1839
```

<210> SEQ ID NO 17
<211> LENGTH: 1839
<212> TYPE: DNA
<213> ORGANISM: Artificial Sequence
<220> FEATURE:
<223> OTHER INFORMATION: Synthetic B.t. toxin gene

<400> SEQUENCE: 17

```
atggacaaca tcccaacat caacgagtgc attccttaca actgcctgag caaccctgag       60
gttgaggtgc tgggtggaga acggattgag actggttaca cacctatcga catctcgttg      120
tcacttaccc aattcctttt gtcagagttc gtgcccggtg ctggattcgt gcttggactt      180
gtcgatatca tttggggaat cttgtcccc tctcaatggg acgcctttct tgtacagata      240
gagcagttaa ttaaccaaag aatagaagaa ttcgctagga accaagccat ctcaaggtta      300
gaaggcctca gcaacctta ccagatctac gcagaatctt ttcgagagtg ggaagcagac      360
ccgaccaatc ctgccttaag agaggagatg cgcattcaat tcaatgacat gaacagcgcg      420
ctgacgaccg caattccgct cttcgccgtt cagaattacc aagttcctct tttatccgtg      480
tacgtgcagg ctgccaacct gcacttgtcg gtgctccgcg atgtctccgt gttcggacaa      540 cggtgggget tgatgccgc aactatcaat agtcgttata atgatctgac taggcttatt      600
ggcaactata ccgattatgc tgttcgctgg tacaacacgg gtctcgaacg tgtctgggga      660
```

```
ccggattcta gagattgggt caggtacaac cagttcaggc gagagttgac actaactgtc      720
ctagacattg tcgctctctt tcccaactac gactctaggc gctacccaat ccgtactgtg      780
tcacaattga cccgggaaat ctacacaaac ccagtcctcg agaacttcga cggtagcttt      840
cgaggctcgg ctcagggcat agagagaagc atcaggtctc cacacctgat ggacatattg      900
aacagtatca cgatctacac cgatgcgcac cgcggttatt actactggtc agggcatcag      960
atcatggcat cacccgttgg gttctctgga ccagaattca ctttcccact ttacgggact     1020
atgggcaatg cagctccaca acaacgtatt gttgctcaac tcggtcaggg cgtgtataga     1080
accttgtcca gcactctata taggagacct ttcaacatcg gcatcaacaa tcaacaattg     1140
tctgtgcttg acgggacaga atttgcctat ggaacctcct caaatctgcc atccgctgtc     1200
tacagaaaga gcggaacagt tgatagcttg gatgagatcc ctccacagaa caacaacgtt     1260
ccacctaggc aagggtttag ccatcgcctt agccatgtgt ccatgttccg ttcaggcttt     1320
agtaatagca gcgttagtat catcagagct ccgatgttct cttggataca tcgtagtgct     1380
gagtttaaca acataattgc atccgatagc attactcaga tcccagctgt caaggggaac     1440
tttctcttta atggttctgt catttcagga ccaggattca ctggaggcga cttggttagg     1500
ctgaattctt ccggcaacaa catccagaat agagggtata ttgaagtgcc cattcacttc     1560
ccatcgacat ctaccagata tcgtgttcgt gtaaggtatg cctctgttac ccctattcac     1620
ctcaacgtca attggggtaa ttcctccatc ttttccaata cagtaccagc gacagctaca     1680
tccttggata atctccaatc tagcgatttc ggttacttcg aaagtgccaa tgccttcacc     1740
tcttccctag gtaacatagt aggtgttaga aatttctccg gaaccgccgg agtgataatc     1800
gaccgcttcg aattcattcc cgttactgca acgctcgag                            1839

<210> SEQ ID NO 18
<211> LENGTH: 1839
<212> TYPE: DNA
<213> ORGANISM: Artificial Sequence
<220> FEATURE:
<223> OTHER INFORMATION: Synthetic B.t. toxin gene

<400> SEQUENCE: 18
atggacaaca atcccaacat caacgagtgc attccttaca actgcctgag caaccctgag       60
gttgaggtgc tgggtggaga acggattgag actggttaca cacctatcga catctcgttg      120
tcacttaccc aattcctttt gtcagagttc gtgcccggtg ctggattcgt gcttggactt      180
gtcgatatca tttggggaat ctttggtccc tctcaatggg acgcctttct tgtacagata      240
gagcagttaa ttaaccaaag aatagaagaa ttcgctagga accaagccat ctcaaggtta      300
gaaggcctca gcaaccttta ccagatctac gcagaatctt ttcgagagtg gaagcagac       360 ccgaccaatc ctgccttaag agaggagatg cgcattcaat tcaatgacat gaacagcgcg      420
ctgacgaccg caattccgct cttcgccgtt cagaattacc aagttcctct tttatccgtg      480
tacgtgcagg ctgccaacct gcacttgtcg gtgctccgcg atgtctccgt gttcggacaa      540
cggtggggct tgatgccgc aactatcaat agtcgttata atgatctgac taggcttatt      600
ggcaactata ccgattatgc tgttcgctgg tacaacacgg tctcgaacg tgtctgggga      660 ccggattcta gagattgggt caggtacaac cagttcaggc gagagttgac actaactgtc     720
ctagacattg tcgctctctt tcccaactac gactctaggc gctacccaat ccgtactgtg      780
tcacaattga cccgggaaat ctacacaaac ccagtcctgg agaacttcga cggtagcttt      840
```

-continued

```
cgaggctcgg ctcagggcat agagagaagc atcaggtctc cacacctgat ggacatattg    900
aacagtatca cgatctacac cgatgcgcac cgcggttatt actactggtc agggcatcag    960
atcatggcat cacccgttgg gttctctgga ccagaattca ctttcccact ttacgggact   1020
atgggcaatg cagctccaca caacgtatt gttgctcaac tcggtcaggg cgtgtataga    1080
accttgtcca gcactctata taggagacct ttcaacatcg gcatcaacaa tcaacaattg   1140
tctgtgcttg acgggacaga atttgcctat ggaacctcct caaatctgcc atccgctgtc   1200
tacagaaaga gcgaacagt tgatagcttg gatgagatcc ctccacagaa caacaacgtt    1260
ccacctaggc aagggtttag ccatcgcctt agccatgtgt ccatgttccg ttcaggcttt   1320
agtaatagca gcgttagtat catcagagct ccgatgttct cttggataca tcgtagtgct   1380
gagtttaaca acataattgc atccgatagc attactcaga tcccagctgt caaggggaac   1440
tttctcttta atggttctgt catttcagga ccaggattca ctggaggcga cttggttagg   1500
ctgaattctt ccggcaacaa catccagaat agagggtata ttgaagtgcc cattcacttc   1560
ccatcgacat ctaccagata tcgtgttcgt gtaaggtatg cctctgttac ccctattcac   1620
ctcaacgtca attggggtaa ttcctccatc ttttccaata cagtaccagc gacagctaca   1680
tccttggata tctccaatc tagcgatttc ggttacttcg aaagtgccaa tgccttcacc    1740
tcttccctag gtaacatagt aggtgttaga aatttctccg gaaccgccgg agtgataatc   1800
gaccgcttcg aattcattcc cgttactgca acgctcgag                           1839
```

<210> SEQ ID NO 19
<211> LENGTH: 1860
<212> TYPE: DNA
<213> ORGANISM: Artificial Sequence
<220> FEATURE:
<223> OTHER INFORMATION: Synthetic B.t. toxin gene

<400> SEQUENCE: 19

```
atggaggaga caatcagaa tcagtgcata ccctacaact gcttgagcaa tcctgaagag     60
gtacttcttg atggagaacg gatctcaact ggtaactcta gcattgacat ctcactgtca    120
cttgttcagt ttcttgtctc caactttgtt ccaggggtg gctttcttgt tggactcata    180
gactttgtgt gggcattgt tggcccatct caatgggatg cctttcttgt acagattgaa    240
cagttgatca atgagaggat agctgagttt gctaggaatg ctgccattgc caatctggaa    300
ggattgggaa acaacttcaa catctatgtg gaagccttca agaatgggga agaagatccc    360
aacaatccag caacccgtac gagagtcatt gatcgctttc ggatacttga tgggctactt    420
gaaagggaca ttccttcgtt tcgaatctcg ggctttgaag tgccgttgct ctccgtgtat    480
gctcaagctg ccaatctgca tcttgcgatt ctaagagatt ctgtgatctt ggagaaaga    540 tggggattga caactatcaa tgtcaatgag aactacaaca gactcatcag acacattgat    600
gagtatgctg atcactgtgc caacacctac aatcgtggtc tcaacaactt accgaagtct   660
acgtatcaag attggatcac ctacaatcga ttgaggaggg atctcacatt gactgtcttg    720
gacattgctg ctttctttcc aaactatgac aacagaagat atcccattca accagttggt    780
caactaacaa gggaagtgta cactgatcca ctcatcaact tcaatccaca gttacaatct    840
gttgctcagt tacctacttt caatgtgatg gaaagctcag ccatcaggaa tccacacttg    900
tttgacattc tcaacaatct taccatcttc actgattggt tcagtgttgg acgcaacttc    960
tactggggtg gacatcgtgt gatctctagc ttgataggtg gaggtaacat cacatctcct    1020
atctatggta gggaggcgaa tcaggagcct ccaagatcct tcactttcaa tggacccgtc   1080
```

```
ttcaggactt tgtccaatcc tactttgcga ttgttacaac aaccatggcc tgctccacca    1140
ttcaacttac gtggtgttga aggagtagag ttctcaacac ccaccaacag cttcacgtat    1200
cgtggaagag gtcaagttga ttcgttgact gagttaccgc ctgaggacaa ctcagttcca    1260
cctcgcgaag gctacagtca tcgtctctgt cacgcaacct tgttcaaag gtctggaaca    1320 ccgttcctga caactggtgt tgtcttctcc tggactcatc gtagcgcaac tcttaccaac    1380
accattgatc cagagaggat caatcagata cctcttgtga aaggcttcag agtttggggg    1440
ggcacttctg tgatcaccgg tccaggattc acaggagggg acattcttcg acgcaacacc    1500
tttggtgact ttgtatctct tcaagtcaac atcaactcac ccatcacaca aagataccgt    1560
ctaaggtttc gttacgcttc cagtagagat gcacgtgtga tagtactcac aggagctgca    1620
tccacaggag ttggaggcca agttagtgtc aacatgcctc ttcagaagac tatggagata    1680
ggggagaact tgacctctag aacctttcgc tacaccgact tcagcaatcc cttctcattc    1740
agagccaatc cagacatcat tgggatcagt gaacaacctc tctttggtgc aggttccatc    1800
agtagcggtg aactgtacat agacaagatt gagatcattc tagctgatgc aacactcgag    1860
```

<210> SEQ ID NO 20
<211> LENGTH: 3489
<212> TYPE: DNA
<213> ORGANISM: Artificial Sequence
<220> FEATURE:
<223> OTHER INFORMATION: Synthetic B.t. toxin gene

<400> SEQUENCE: 20

```
atggaggaga caatcagaa tcagtgcata ccctacaact gcttgagcaa tcctgaagag      60
gtacttcttg atggagaacg gatctcaact ggtaactcta gcattgacat ctcactgtca    120
cttgttcagt ttcttgtctc caactttgtt ccagggggtg gctttcttgt tggactcata    180
gactttgtgt ggggcattgt tggcccatct caatgggatg cctttcttgt acagattgaa    240
cagttgatca atgagaggat agctgagttt gctaggaatg ctgccattgc caatctggaa    300
ggattgggaa acaacttcaa catctatgtg gaagccttca agaatgggga agaagatccc    360
aacaatccag caacccgtac gagagtcatt gatcgctttc ggatacttga tgggctactt    420
gaaagggaca ttccttcgtt tcgaatctcg ggctttgaag tgccgttgct ctccgtgtat    480
gctcaagctg ccaatctgca tcttgcgatt ctaagagatt ctgtgatctt ggagaaaga    540 tggggattga caactatcaa tgtcaatgag aactacaaca gactcatcag acacattgat    600
gagtatgctg atcactgtgc caacacctac aatcgtggtc tcaacaactt accgaagtct    660
acgtatcaag attggatcac ctacaatcga ttgaggaggg atctcacatt gactgtcttg    720
gacattgctg ctttctttcc aaactatgac aacagaagat atcccattca accagttggt    780
caactaacaa gggaagtgta cactgatcca ctcatcaact tcaatccaca gttacaatct    840
gttgctcagt tacctacttt caatgtgatg gaaagctcag ccatcaggaa tccacacttg    900
tttgacattc tcaacaatct taccatcttc actgattggt tcagtgttgg acgcaacttc    960
tactggggtg gacatcgtgt gatctctagc ttgataggtg aggtaacat cacatctcct   1020 atctatggta gggaggcgaa tcaggagcct ccaagatcct tcactttcaa tggacccgtc   1080
ttcaggactt tgtccaatcc tactttgcga ttgttacaac aaccatggcc tgctccacca   1140
ttcaacttac gtggtgttga aggagtagag ttctcaacac ccaccaacag cttcacgtat   1200
cgtggaagag gtcaagttga ttcgttgact gagttaccgc ctgaggacaa ctcagttcca   1260
```

-continued

```
cctcgcgaag gctacagtca tcgtctctgt cacgcaacct ttgttcaaag gtctggaaca    1320
ccgttcctga caactggtgt tgtcttctcc tggactcatc gtagcgcaac tcttaccaac    1380
accattgatc cagagaggat caatcagata cctcttgtga aaggcttcag agtttggggg    1440
ggcacttctg tgatcaccgg tccaggattc acaggagggg acattcttcg acgcaacacc    1500
tttggtgact ttgtatctct tcaagtcaac atcaactcac ccatcacaca agataccgt     1560
ctaaggtttc gttacgcttc cagtagagat gcacgtgtga tagtactcac aggagctgca    1620
tccacaggag ttggaggcca agttagtgtc aacatgcctc ttcagaagac tatggagata    1680
ggggagaact tgacctctag aacctttcgc tacaccgact tcagcaatcc cttctcattc    1740
agagccaatc cagacatcat tgggatcagt gaacaacctc tctttggtgc aggttccatc    1800
agtagcggtg aactgtacat agacaagatt gagatcattc tagctgatgc aacactcgag    1860
gcagagtctg acttggaaag agcacagaag gcggtgaatg ctctgttcac ttcgtccaat    1920
cagattgggc tcaagacaga tgtgactgac tatcacatcg atcgcgtttc caaccttgtt    1980
gagtgcctct ctgatgagtt ctgtttggat gagaagaagg agttgtccga aaggtcaaa     2040
catgctaagc gacttagtga tgagcggaac ttgcttcaag atcccaactt tcgcgggatc    2100
aacaggcaac tagatcgtgg atggagggga agtacggaca tcaccattca aggaggtgat    2160
gatgtgttca aggagaacta tgttacgctc ttgggtacct ttgatgagtg ctatccaaca    2220
tacctgtacc agaagataga tgaatcgaaa ctcaaagcct acacaagata ccagttgaga    2280
ggttacatcg aggacagtca agaccttgag atctacctca tcagatacaa cgccaaacat    2340
gagacagtca atgtgcctgg gacgggttca ctctggccac tttcagcccc aagtcccatc    2400
ggcaagtgtg cccatcactc acaccacttc tccttggaca tagacgttgg ctgtaccgac    2460
ctgaacgaag acctcggtgt gtgggtgatc ttcaagatca agactcaaga tggccatgcc    2520
aggctaggca atctggagtt tctagaagag aaaccacttg ttggagaagc cctcgctaga    2580
gtgaagaggg ctgagaagaa gtggagggac aagagagaga agttggaatg ggaaacaaac    2640
attgtgtaca aagaagccaa agaaagcgtt gacgctctgt ttgtgaactc tcagtatgat    2700
aggctccaag ctgataccaa catagctatg attcatgctg cagacaaacg cgttcatagc    2760
attcgggaag cttaccttcc tgaacttagc gtgattccgg gtgtcaatgc tgctatcttt    2820
gaagagttag aagggcgcat cttcactgca ttctccttgt atgatgcgag gaatgtcatc    2880
aagaatggtg acttcaacaa tggcctatcc tgctggaatg tgaaagggca cgtagatgta    2940
gaagaacaga acaatcaccg ctctgtcctt gttgttcctg agtgggaagc agaagtttca    3000
caagaagttc gtgtctgtcc tggtcgtggc tacattcttc gtgttaccgc gtacaaagaa    3060
ggatacggag aaggttgcgt caccatacac gagattgaga acaacaccga cgagctgaag    3120
ttcagcaact cgctcgagga ggaagtctac ccaaacaaca ccgtaacttg caatgactac    3180
actgcgactc aagaggagta tgagggtact tacacttctc gcaatcgagg atacgatgga    3240
gcctatgaga gcaactcttc tgtacccgct gactatgcat cagcctatga ggagaaggct    3300
tacaccgatg gacgtaggga caatccttgc gaatctaaca gaggctatgg ggactacaca    3360
ccgttaccag ccggctatgt caccaaagag ttagagtact ttccagaaac cgacaaggtt    3420
tggattgaga ttggagaaac ggaaggaaca ttcattgttg atagcgtgga gttacttctg    3480
atggaggaa                                                            3489
```

<210> SEQ ID NO 21
<211> LENGTH: 1163

<212> TYPE: PRT
<213> ORGANISM: Artificial Sequence
<220> FEATURE:
<223> OTHER INFORMATION: Toxin encoded by synthetic B.t. gene

<400> SEQUENCE: 21

Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

-continued

```
Gly Val Glu Gly Val Glu Phe Ser Thr Pro Thr Asn Ser Phe Thr Tyr
385                 390                 395                 400

Arg Gly Arg Gly Gln Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Leu Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Arg Val
                645                 650                 655

Ser Asn Leu Val Glu Cys Leu Ser Asp Glu Phe Cys Leu Asp Glu Lys
            660                 665                 670

Lys Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Leu
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Leu Gly Thr Phe Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Gln Leu Arg Gly Tyr Ile Glu Asp Ser Gln Asp
        755                 760                 765

Leu Glu Ile Tyr Leu Ile Arg Tyr Asn Ala Lys His Glu Thr Val Asn
    770                 775                 780

Val Pro Gly Thr Gly Ser Leu Trp Pro Leu Ser Ala Pro Ser Pro Ile
785                 790                 795                 800

Gly Lys Cys Ala His His Ser His His Phe Ser Leu Asp Ile Asp Val
```

```
                        805                 810                 815
Gly Cys Thr Asp Leu Asn Glu Asp Leu Gly Val Trp Val Ile Phe Lys
                820                 825                 830

Ile Lys Thr Gln Asp Gly His Ala Arg Leu Gly Asn Leu Glu Phe Leu
                835                 840                 845

Glu Glu Lys Pro Leu Val Gly Glu Ala Leu Ala Arg Val Lys Arg Ala
            850                 855                 860

Glu Lys Lys Trp Arg Asp Lys Arg Glu Lys Leu Glu Trp Glu Thr Asn
865                 870                 875                 880

Ile Val Tyr Lys Glu Ala Lys Glu Ser Val Asp Ala Leu Phe Val Asn
                885                 890                 895

Ser Gln Tyr Asp Arg Leu Gln Ala Asp Thr Asn Ile Ala Met Ile His
            900                 905                 910

Ala Ala Asp Lys Arg Val His Ser Ile Arg Glu Ala Tyr Leu Pro Glu
            915                 920                 925

Leu Ser Val Ile Pro Gly Val Asn Ala Ala Ile Phe Glu Glu Leu Glu
        930                 935                 940

Gly Arg Ile Phe Thr Ala Phe Ser Leu Tyr Asp Ala Arg Asn Val Ile
945                 950                 955                 960

Lys Asn Gly Asp Phe Asn Asn Gly Leu Ser Cys Trp Asn Val Lys Gly
                965                 970                 975

His Val Asp Val Glu Glu Gln Asn Asn His Arg Ser Val Leu Val Val
            980                 985                 990

Pro Glu Trp Glu Ala Glu Val Ser Gln Glu Val Arg Val Cys Pro Gly
        995                 1000                1005

Arg Gly Tyr Ile Leu Arg Val Thr Ala Tyr Lys Glu Gly Tyr Gly Glu
        1010                1015                1020

Gly Cys Val Thr Ile His Glu Ile Glu Asn Asn Thr Asp Glu Leu Lys
1025                1030                1035                1040

Phe Ser Asn Cys Val Glu Glu Val Tyr Pro Asn Asn Thr Val Thr
                1045                1050                1055

Cys Asn Asp Tyr Thr Ala Thr Gln Glu Glu Tyr Glu Gly Thr Tyr Thr
            1060                1065                1070

Ser Arg Asn Arg Gly Tyr Asp Gly Ala Tyr Glu Ser Asn Ser Ser Val
            1075                1080                1085

Pro Ala Asp Tyr Ala Ser Ala Tyr Glu Glu Lys Ala Tyr Thr Asp Gly
        1090                1095                1100

Arg Arg Asp Asn Pro Cys Glu Ser Asn Arg Gly Tyr Gly Asp Tyr Thr
1105                1110                1115                1120

Pro Leu Pro Ala Gly Tyr Val Thr Lys Glu Leu Glu Tyr Phe Pro Glu
                1125                1130                1135

Thr Asp Lys Val Trp Ile Glu Ile Gly Glu Thr Glu Gly Thr Phe Ile
                1140                1145                1150

Val Asp Ser Val Glu Leu Leu Leu Met Glu Glu
                1155                1160

<210> SEQ ID NO 22
<211> LENGTH: 3558
<212> TYPE: DNA
<213> ORGANISM: Artificial Sequence
<220> FEATURE:
<223> OTHER INFORMATION: Synthetic B.t. toxin gene

<400> SEQUENCE: 22
atgacttcta acagaaagaa cgagaacgag atcatcaacg ctctttctat cccagctgtt    60
```

-continued

```
tctaaccatt ctgctcagat gaacctttct actgatgcta gaatcgagga ttctctttgc    120
attgctgagg gaaacaacat tgatccattc gtttctgctt ctactgttca aactggaatc    180
aacattgctg gaagaatcct tggagttctt ggagttccat cgctggaca gattgcttct    240 ttctactctt tccttgttgg agagctttgg cctaggggaa gagatccttg ggagatcttc    300
cttgagcatg ttgagcagtt gattcgtcaa caagttactg agaacactag agatactgct    360
cttgctagac ttcaaggact tggaaactct ttcagagctt accaacaatc tcttgaggat    420
tggcttgaga acagagatga tgctagaact agatctgtgt tgtacactca gtacattgct    480
cttgagcttg acttcttgaa cgctatgcca ttgttcgcta tcagaaacca agaggttcca    540
cttctcatgg tgtacgctca agctgctaac cttcatcttc ttcttcttag agatgctagc    600
ttgttcggat ctgagttcgg acttacttct caagagattc aaagatacta cgagagacaa    660
gttgagaaga ctagagagta ctctgactac tgcgctaggt ggtacaacac tggattgaac    720
aaccttagag gaactaacgc tgagtcttgg cttagataca accagttcag aagagatctt    780
actcttggag ttcttgatct tgttgccttg ttcccatctt acgatactag agtgtaccct    840
atgaacactt ctgctcaact tactagagag atctacactg atccaatcgg aagaactaac    900
gctccatctg gattcgcttc tactaactgg ttcaacaaca acgctccatc tttctctgct    960
atcgaggctg cagtgatcag accaccacat cttcttgact cccagagca acttactatc    1020 ttctctgttc tttctagatg gtctaacact cagtacatga actactgggt tggacataga    1080
cttgagtcta gaactatcag aggatctctt tctacttcta ctcatggaaa cactaacact    1140
tctatcaacc cagttactct tcagttcact tctagagatg tgtacagaac tgagtctttc    1200
gctggaatca acattcttct tactactcca gtgaacggag ttccttgggc tagattcaac    1260
tggagaaacc cattgaactc tcttagaggt tccttgttgt acaccattgg atacactgga    1320
gttggtaccc agttgttcga ttctgagact gagcttccac cagagactac tgagagacca    1380
aactacgagt cttactctca tagacttttct aacattcgtt tgatctctgg aaacactctt    1440
agagctccag tgtactcttg gactcataga tctgctgata gaactaacac catctcttct    1500
gattctatca ctcagattcc acttgtgaag tctttcaact tgaactctgg aacttctgtt    1560
gtttctggac caggattcac tggaggagac atcatcagaa ctaacgtgaa cggatctgtt    1620 cttttctatgg gattgaactt caacaacact tctcttcaaa gatacagagt tagagttaga    1680
tacgctgctt ctcaaactat ggttcttaga gttactgttg gaggatctac tactttcgat    1740
caaggattcc catctactat gtctgctaac gagtctctta cttctcaatc tttcagattc    1800
gctgagttcc cagttggaat tctgcttct ggatctcaaa ctgctggaat ctctatctct    1860
aacaacgctg gaagacaaac tttccacttc gacaagattg agttcattcc aatcactgct    1920
actctcgagg cagagtctga cttggaaaga gcacagaagg cggtgaatgc tctgttcact    1980
tcgtccaatc agattgggct caagacagat gtgactgact atcacatcga tcgcgtttcc    2040
aaccttgttg agtgcctctc tgatgagttc tgtttggatg agaagaagga gttgtccgag    2100
aaggtcaaac atgctaagcg acttagtgat gagcggaact tgcttcaaga tcccaacttt    2160
cgcgggatca acaggcaact agatcgtgga tggaggggaa gtacggacat caccattcaa    2220
ggaggtgatg atgtgttcaa ggagaactat gttacgctct gggtaccttt tgatgagtgc    2280
tatccaacat acctgtacca gagatagat gaatcgaaac tcaaagccta cacaagatac    2340
cagttgagag gttacatcga ggacagtcaa gaccttgaga tctacctcat cagatacaac    2400
```

```
gccaaacatg agacagtcaa tgtgcctggg acgggttcac tctggccact ttcagcccca    2460
agtcccatcg gcaagtgtgc ccatcactca caccacttct ccttggacat agacgttggc    2520
tgtaccgacc tgaacgaaga cctcggtgtg tgggtgatct tcaagatcaa gactcaagat    2580
ggccatgcca ggctaggcaa tctggagttt ctagaagaga accacttgt tggagaagcc     2640 ctcgctagag tgaagagggc tgagaagaag tggagggaca agagagagaa gttggaatgg    2700
gaaacaaaca ttgtgtacaa agaagccaaa gaaagcgttg acgctctgtt tgtgaactct    2760
cagtatgata ggctccaagc tgataccaac atagctatga ttcatgctgc agacaaacgc    2820
gttcatagca ttcgggaagc ttaccttcct gaacttagcg tgattccggg tgtcaatgct    2880
gctatctttg aagagttaga agggcgcatc ttcactgcat tctccttgta tgatgcgagg    2940
aatgtcatca agaatggtga cttcaacaat ggcctatcct gctggaatgt gaagggcac     3000 gtagatgtag aagaacagaa caatcaccgc tctgtccttg ttgttcctga gtgggaagca    3060
gaagtttcac aagaagttcg tgtctgtcct ggtcgtggct acattcttcg tgttaccgcg    3120
tacaaagaag gatacggaga aggttgcgtc accatacacg agattgagaa caacaccgac    3180
gagctgaagt tcagcaactg cgtcgaggag gaagtctacc caaacaacac cgtaacttgc    3240
aatgactaca ctgcgactca agaggagtat gagggtactt acacttctcg caatcgagga    3300
tacgatggag cctatgagag caactcttct gtacccgctg actatgcatc agcctatgag    3360
gagaaggctt acaccgatgg acgtagggac aatccttgcg aatctaacag aggctatggg    3420
gactacacac cgttaccagc cggctatgtc accaaagagt tagagtactt tccagaaacc    3480
gacaaggttt ggattgagat tggagaaacg gaaggaacat tcattgttga tagcgtggag    3540
ttacttctga tggaggaa                                                    3558
```

<210> SEQ ID NO 23
<211> LENGTH: 1186
<212> TYPE: PRT
<213> ORGANISM: Artificial Sequence
<220> FEATURE:
<223> OTHER INFORMATION: Toxin encoded by synthetic B.t. gene

<400> SEQUENCE: 23

```
Met Thr Ser Asn Arg Lys Asn Glu Asn Glu Ile Ile Asn Ala Leu Ser
 1               5                  10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
               100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160
```

-continued

```
Leu Glu Leu Asp Phe Leu Asn Ala Met Pro Leu Phe Ala Ile Arg Asn
            165                 170                 175
Gln Glu Val Pro Leu Leu Met Val Tyr Ala Gln Ala Ala Asn Leu His
        180                 185                 190
Leu Leu Leu Leu Arg Asp Ala Ser Leu Phe Gly Ser Glu Phe Gly Leu
        195                 200                 205
Thr Ser Gln Glu Ile Gln Arg Tyr Tyr Glu Arg Gln Val Glu Lys Thr
        210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
            245                 250                 255
Arg Arg Asp Leu Thr Leu Gly Val Leu Asp Leu Val Ala Leu Phe Pro
            260                 265                 270
Ser Tyr Asp Thr Arg Val Tyr Pro Met Asn Thr Ser Ala Gln Leu Thr
        275                 280                 285
Arg Glu Ile Tyr Thr Asp Pro Ile Gly Arg Thr Asn Ala Pro Ser Gly
        290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
            325                 330                 335
Gln Leu Thr Ile Phe Ser Val Leu Ser Arg Trp Ser Asn Thr Gln Tyr
            340                 345                 350
Met Asn Tyr Trp Val Gly His Arg Leu Glu Ser Arg Thr Ile Arg Gly
        355                 360                 365
Ser Leu Ser Thr Ser Thr His Gly Asn Thr Asn Thr Ser Ile Asn Pro
370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
            405                 410                 415
Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
        435                 440                 445
Glu Thr Glu Leu Pro Pro Glu Thr Thr Glu Arg Pro Asn Tyr Glu Ser
        450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
            485                 490                 495
Thr Ile Ser Ser Asp Ser Ile Thr Gln Ile Pro Leu Val Lys Ser Phe
            500                 505                 510
Asn Leu Asn Ser Gly Thr Ser Val Val Ser Gly Pro Gly Phe Thr Gly
            515                 520                 525
Gly Asp Ile Ile Arg Thr Asn Val Asn Gly Ser Val Leu Ser Met Gly
        530                 535                 540
Leu Asn Phe Asn Asn Thr Ser Leu Gln Arg Tyr Arg Val Arg Val Arg
545                 550                 555                 560
Tyr Ala Ala Ser Gln Thr Met Val Leu Arg Val Thr Val Gly Gly Ser
            565                 570                 575
```

-continued

```
Thr Thr Phe Asp Gln Gly Phe Pro Ser Thr Met Ser Ala Asn Glu Ser
            580                 585                 590

Leu Thr Ser Gln Ser Phe Arg Phe Ala Glu Phe Pro Val Gly Ile Ser
        595                 600                 605

Ala Ser Gly Ser Gln Thr Ala Gly Ile Ser Ile Ser Asn Asn Ala Gly
    610                 615                 620

Arg Gln Thr Phe His Phe Asp Lys Ile Glu Phe Ile Pro Ile Thr Ala
625                 630                 635                 640

Thr Leu Glu Ala Glu Ser Asp Leu Glu Arg Ala Gln Lys Ala Val Asn
                645                 650                 655

Ala Leu Phe Thr Ser Ser Asn Gln Ile Gly Leu Lys Thr Asp Val Thr
            660                 665                 670

Asp Tyr His Ile Asp Arg Val Ser Asn Leu Val Glu Cys Leu Ser Asp
        675                 680                 685

Glu Phe Cys Leu Asp Glu Lys Lys Glu Leu Ser Glu Lys Val Lys His
    690                 695                 700

Ala Lys Arg Leu Ser Asp Glu Arg Asn Leu Leu Gln Asp Pro Asn Phe
705                 710                 715                 720

Arg Gly Ile Asn Arg Gln Leu Asp Arg Gly Trp Arg Gly Ser Thr Asp
                725                 730                 735

Ile Thr Ile Gln Gly Gly Asp Asp Val Phe Lys Glu Asn Tyr Val Thr
            740                 745                 750

Leu Leu Gly Thr Phe Asp Glu Cys Tyr Pro Thr Tyr Leu Tyr Gln Lys
        755                 760                 765

Ile Asp Glu Ser Lys Leu Lys Ala Tyr Thr Arg Tyr Gln Leu Arg Gly
    770                 775                 780

Tyr Ile Glu Asp Ser Gln Asp Leu Glu Ile Tyr Leu Ile Arg Tyr Asn
785                 790                 795                 800

Ala Lys His Glu Thr Val Asn Val Pro Gly Thr Gly Ser Leu Trp Pro
                805                 810                 815

Leu Ser Ala Pro Ser Pro Ile Gly Lys Cys Ala His His Ser His His
            820                 825                 830

Phe Ser Leu Asp Ile Asp Val Gly Cys Thr Asp Leu Asn Glu Asp Leu
        835                 840                 845

Gly Val Trp Val Ile Phe Lys Ile Lys Thr Gln Asp Gly His Ala Arg
    850                 855                 860

Leu Gly Asn Leu Glu Phe Leu Glu Glu Lys Pro Leu Val Gly Glu Ala
865                 870                 875                 880

Leu Ala Arg Val Lys Arg Ala Glu Lys Lys Trp Arg Asp Lys Arg Glu
                885                 890                 895

Lys Leu Glu Trp Glu Thr Asn Ile Val Tyr Lys Glu Ala Lys Glu Ser
            900                 905                 910

Val Asp Ala Leu Phe Val Asn Ser Gln Tyr Asp Arg Leu Gln Ala Asp
        915                 920                 925

Thr Asn Ile Ala Met Ile His Ala Ala Asp Lys Arg Val His Ser Ile
    930                 935                 940

Arg Glu Ala Tyr Leu Pro Glu Leu Ser Val Ile Pro Gly Val Asn Ala
945                 950                 955                 960

Ala Ile Phe Glu Glu Leu Glu Gly Arg Ile Phe Thr Ala Phe Ser Leu
                965                 970                 975

Tyr Asp Ala Arg Asn Val Ile Lys Asn Gly Asp Phe Asn Asn Gly Leu
            980                 985                 990

Ser Cys Trp Asn Val Lys Gly His Val Asp Val Glu Glu Gln Asn Asn
```

```
                 995                1000                    1005
     His Arg Ser Val Leu Val Val Pro Glu Trp Glu Ala Glu Val Ser Gln
             1010                1015                    1020
     Glu Val Arg Val Cys Pro Gly Arg Gly Tyr Ile Leu Arg Val Thr Ala
     1025                1030                    1035                1040
     Tyr Lys Glu Gly Tyr Gly Glu Gly Cys Val Thr Ile His Glu Ile Glu
                     1045                1050                    1055
     Asn Asn Thr Asp Glu Leu Lys Phe Ser Asn Cys Val Glu Glu Glu Val
                 1060                1065                    1070
     Tyr Pro Asn Asn Thr Val Thr Cys Asn Asp Tyr Thr Ala Thr Gln Glu
             1075                1080                    1085
     Glu Tyr Glu Gly Thr Tyr Thr Ser Arg Asn Arg Gly Tyr Asp Gly Ala
             1090                1095                    1100
     Tyr Glu Ser Asn Ser Ser Val Pro Ala Asp Tyr Ala Ser Ala Tyr Glu
     1105                1110                    1115                1120
     Glu Lys Ala Tyr Thr Asp Gly Arg Arg Asp Asn Pro Cys Glu Ser Asn
                     1125                1130                    1135
     Arg Gly Tyr Gly Asp Tyr Thr Pro Leu Pro Ala Gly Tyr Val Thr Lys
                 1140                1145                    1150
     Glu Leu Glu Tyr Phe Pro Glu Thr Asp Lys Val Trp Ile Glu Ile Gly
                 1155                1160                    1165
     Glu Thr Glu Gly Thr Phe Ile Val Asp Ser Val Glu Leu Leu Leu Met
         1170                1175                    1180
     Glu Glu
     1185

<210> SEQ ID NO 24
<211> LENGTH: 1929
<212> TYPE: DNA
<213> ORGANISM: Artificial Sequence
<220> FEATURE:
<223> OTHER INFORMATION: Synthetic B.t. toxin gene

<400> SEQUENCE: 24
atgacttcta acagaaagaa cgagaacgag atcatcaacg ctctttctat cccagctgtt      60
tctaaccatt ctgctcagat gaacctttct actgatgcta atcgagga ttctctttgc       120 attgctgagg gaaacaacat tgatccattc gtttctgctt ctactgttca aactggaatc     180
aacattgctg gaagaatcct ggagttcttc ggagttccat cgctggaca gattgcttct     240 ttctactctt tccttgttgg agagctttgg cctagggaa gagatccttg ggagatcttc     300
cttgagcatg ttgagcagtt gattcgtcaa caagttactg agaacactag agatactgct     360
cttgctagac ttcaaggact tggaaactct ttcagagctt accaacaatc tcttgaggat     420
tggcttgaga cagagatga tgctagaact agatctgtgt tgtacactca gtacattgct     480
cttgagcttg acttcttgaa cgctatgcca ttgttcgcta tcagaaacca agaggttcca     540
cttctcatgg tgtacgctca agctgctaac cttcatcttc ttcttcttag atgctagc     600 ttgttcggat ctgagttcgg acttacttct caagagattc aaagatacta cgagagacaa     660
gttgagaaga ctagagagta ctctgactac tgcgctaggt ggtacaacac tggattgaac     720
aaccttagag gaactaacgc tgagtcttgg cttagataca ccagttcag aagagatctt     780 actcttggag ttcttgatct tgttgccttg ttcccatctt cgatactag agtgtaccct     840 atgaacactt ctgctcaact tactagagag atctacactg atccaatcgg aagaactaac     900
gctccatctg gattcgcttc tactaactgg ttcaacaaca cgctccatc tttctctgct     960
```

-continued

```
atcgaggctg cagtgatcag accaccacat cttcttgact tcccagagca acttactatc      1020
ttctctgttc tttctagatg gtctaacact cagtacatga actactgggt tggacataga      1080
cttgagtcta gaactatcag aggatctctt tctacttcta ctcatggaaa cactaacact      1140
tctatcaacc cagttactct tcagttcact tctagagatg tgtacagaac tgagtctttc      1200
gctggaatca acattcttct tactactcca gtgaacggag ttccttgggc tagattcaac      1260
tggagaaacc cattgaactc tcttagaggt tccttgttgt acaccattgg atacactgga      1320
gttggtaccc agttgttcga ttctgagact gagcttccac cagagactac tgagagacca      1380
aactacgagt cttactctca tagactttct aacattcgtt tgatctctgg aaacactctt      1440
agagctccag tgtactcttg gactcataga tctgctgata gaactaacac catctcttct      1500
gattctatca ctcagattcc acttgtgaag tctttcaact tgaactctgg aacttctgtt      1560
gtttctggac caggattcac tggaggagac atcatcagaa ctaacgtgaa cggatctgtt      1620
ctttctatgg gattgaactt caacaacact tctcttcaaa gatacagagt tagagttaga      1680
tacgctgctt ctcaaactat ggttcttaga gttactgttg gaggatctac tactttcgat      1740
caaggattcc catctactat gtctgctaac gagtctctta cttctcaatc tttcagattc      1800
gctgagttcc cagttggaat ctctgcttct ggatctcaaa ctgctggaat ctctatctct      1860
aacaacgctg gaagacaaac tttccacttc gacaagattg agttcattcc aatcactgct      1920
actctcgag                                                              1929
```

<210> SEQ ID NO 25
<211> LENGTH: 643
<212> TYPE: PRT
<213> ORGANISM: Artificial Sequence
<220> FEATURE:
<223> OTHER INFORMATION: Toxin encoded by synthetic B.t. gene
<220> FEATURE:
<223> OTHER INFORMATION: Toxin encoded by synthetic B.t. gene

<400> SEQUENCE: 25

```
Met Thr Ser Asn Arg Lys Asn Glu Asn Glu Ile Ile Asn Ala Leu Ser
 1               5                  10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
    65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
    145                 150                 155                 160

Leu Glu Leu Asp Phe Leu Asn Ala Met Pro Leu Phe Ala Ile Arg Asn
                165                 170                 175
```

```
Gln Glu Val Pro Leu Leu Met Val Tyr Ala Gln Ala Asn Leu His
            180                 185                 190

Leu Leu Leu Leu Arg Asp Ala Ser Leu Phe Gly Ser Glu Phe Gly Leu
                195                 200                 205

Thr Ser Gln Glu Ile Gln Arg Tyr Tyr Glu Arg Gln Val Glu Lys Thr
            210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ser Phe
            500                 505                 510

Asn Leu Asn Ser Gly Thr Ser Val Val Ser Gly Pro Gly Phe Thr Gly
            515                 520                 525

Gly Asp Ile Ile Arg Thr Asn Val Asn Gly Ser Val Leu Ser Met Gly
            530                 535                 540

Leu Asn Phe Asn Asn Thr Ser Leu Gln Arg Tyr Arg Val Arg Val Arg
545                 550                 555                 560

Tyr Ala Ala Ser Gln Thr Met Val Leu Arg Val Thr Val Gly Gly Ser
                565                 570                 575

Thr Thr Phe Asp Gln Gly Phe Pro Ser Thr Met Ser Ala Asn Glu Ser
            580                 585                 590
```

-continued

```
Leu Thr Ser Gln Ser Phe Arg Phe Ala Glu Phe Pro Val Gly Ile Ser
            595                 600                 605

Ala Ser Gly Ser Gln Thr Ala Gly Ile Ser Ile Ser Asn Asn Ala Gly
        610                 615                 620

Arg Gln Thr Phe His Phe Asp Lys Ile Glu Phe Ile Pro Ile Thr Ala
625                 630                 635                 640

Thr Leu Glu

<210> SEQ ID NO 26
<211> LENGTH: 1965
<212> TYPE: DNA
<213> ORGANISM: Artificial Sequence
<220> FEATURE:
<223> OTHER INFORMATION: Synthetic B.t. toxin gene

<400> SEQUENCE: 26
atgaaccgca acaacccgaa cgagtacgag atcatcgacg ccccgtactg cggctgcccg      60
tccgacgacg acgtgcgcta cccgctcgcc tccgacccga cgccgccttc cagaacatg     120 aactacaagg agtacctcca gacctacgac ggcgactaca ccggctccct catcaacccg     180
aacctctcca tcaacccgcg cgacgtcctc cagaccggca tcaacatcgt ggggcgcatc     240
ctcggcttcc tgggcgtgcc gttcgccggc agctcgtga ccttctacac cttcctcctc      300
aaccagctct ggccgaccaa cgacaacgcc gtgtgggagg cgttcatggc ccagatcgag     360
gagctcatcg accagaagat ctccgcccag gtggtgcgca acgccctcga cgacctcacc     420
ggcctccacg actactacga ggagtacctc gcggcgctgg aggagtggct ggagaggccg     480
aacggcgctc gcgccaacct cgtgaccgag aggttcgaga acctccacac cgccttcgtg     540
acccgcatgc cgtcgttcgg gacggggcca gggagccaga gggacgccgt cgcgctcctc     600
accgtgtacg cccaggccgc caactccac ctcctcctcc tcaaggacgc cgagatctac      660
ggcgcccgct ggggcctcca gcagggccag atcaacctct acttcaacgc ccagcaggag     720
cgcacccgca tctacaccaa ccactgcgtg gagacctaca accgcggcct ggaggacgtg     780
cgcggcacca acaccgagtc ctggctcaac taccaccgct tccgcaggga gatgaccctc     840
atggcgatgg acctcgtggc cctcttcccg ttctacaacg tgcgccagta cccgaacggc     900
gccaacccgc agctcacccg cgagatctac accgacccga tcgtgtacaa cccgccggcc     960
aaccagggca tctgccgccg ctgggggcaac aacccgtaca acaccttctc cgagctggag    1020
aacgccttca tcaggccgcc gcacctcttc gagcgcctca accgcctcac catctcccgc    1080
aaccgctaca ccgccccgac caccaactcc ttcctcgact actggtccgg ccacaccctg    1140
cagtcccagc acgccaacaa cccgaccacc tacgagacct cctacggcca gatcacctcc    1200
aacacccgcc tcttcaacac caccaacggc gccagggcca tcgactccag ggcgcgcaat    1260
ttcggcaacc tctacgccaa cctctacggc gtgtcctccc tcaacatctt cccgaccggc    1320
gtgatgtccg agatcaccaa cgccgccaac acctgccgcc aggacctcac caccaccgag    1380
gagctcccgc tggagaacaa caacttcaac ctcctctccc acgtgacctt cctccgcttc    1440
aacaccaccc agggcggccc actcgcgacg ctggggttcg tcccgaccta cgtgtggacc    1500
cgggaggacg tcgacttcac caacaccatc accgccgacc gcatcacgca gctcccgtgg    1560
gtcaaggcct ccgagatcgg cggcggcacg acggtcgtca aggggccggg cttcaccggg    1620
ggggacatcc tccgccgcac cgacggcggc gctgtgggca ccatccgcgc caacgtgaac    1680
gccccgctca cccagcagta ccgcatccgc ctccgctacg cctccaccac ctccttcgtg    1740
```

```
gtgaacctct tcgtgaacaa ctccgctgcc ggcttcaccc tcccgtccac gatggcccag    1800
aacggctccc tcacctacga gtccttcaac accctggagg tgacgcacac catccgcttc    1860
tcccagtccg acaccaccct ccgcctcaac atcttcccgt ccatcagcgg ccaggaggtg    1920
tacgtggaca agctcgagat cgtgccgatc aacccgaccc gcgag                    1965
```

<210> SEQ ID NO 27
<211> LENGTH: 655
<212> TYPE: PRT
<213> ORGANISM: Artificial Sequence
<220> FEATURE:
<223> OTHER INFORMATION: Toxin encoded by synthetic B.t. gene

<400> SEQUENCE: 27

```
Met Asn Arg Asn Asn Pro Asn Glu Tyr Glu Ile Ile Asp Ala Pro Tyr
  1               5                  10                  15

Cys Gly Cys Pro Ser Asp Asp Val Arg Tyr Pro Leu Ala Ser Asp
             20                  25                  30

Pro Asn Ala Ala Phe Gln Asn Met Asn Tyr Lys Glu Tyr Leu Gln Thr
         35                  40                  45

Tyr Asp Gly Asp Tyr Thr Gly Ser Leu Ile Asn Pro Asn Leu Ser Ile
 50                  55                  60

Asn Pro Arg Asp Val Leu Gln Thr Gly Ile Asn Ile Val Gly Arg Ile
 65                  70                  75                  80

Leu Gly Phe Leu Gly Val Pro Phe Ala Gly Gln Leu Val Thr Phe Tyr
                 85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asp Gln Lys Ile Ser
        115                 120                 125

Ala Gln Val Val Arg Asn Ala Leu Asp Asp Leu Thr Gly Leu His Asp
    130                 135                 140

Tyr Tyr Glu Glu Tyr Leu Ala Ala Leu Glu Glu Trp Leu Glu Arg Pro
145                 150                 155                 160

Asn Gly Ala Arg Ala Asn Leu Val Thr Gln Arg Phe Glu Asn Leu His
                165                 170                 175

Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Gln Gln Gly Gln Ile Asn Leu Tyr Phe Asn Ala Gln Gln Glu
225                 230                 235                 240

Arg Thr Arg Ile Tyr Thr Asn His Cys Val Glu Thr Tyr Asn Arg Gly
                245                 250                 255

Leu Glu Asp Val Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
        275                 280                 285

Phe Pro Phe Tyr Asn Val Arg Gln Tyr Pro Asn Gly Ala Asn Pro Gln
    290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
```

```
                    325                 330                 335
Ser Glu Leu Glu Asn Ala Phe Ile Arg Pro Pro His Leu Phe Glu Arg
                340                 345             350
Leu Asn Arg Leu Thr Ile Ser Arg Asn Arg Tyr Thr Ala Pro Thr Thr
                355                 360             365
Asn Ser Phe Leu Asp Tyr Trp Ser Gly His Thr Leu Gln Ser Gln His
                370             375                 380
Ala Asn Asn Pro Thr Thr Tyr Glu Thr Ser Tyr Gly Gln Ile Thr Ser
385                 390                 395                 400
Asn Thr Arg Leu Phe Asn Thr Thr Asn Gly Ala Arg Ala Ile Asp Ser
                    405                 410                 415
Arg Ala Arg Asn Phe Gly Asn Leu Tyr Ala Asn Leu Tyr Gly Val Ser
                420                 425                 430
Ser Leu Asn Ile Phe Pro Thr Gly Val Met Ser Glu Ile Thr Asn Ala
                435                 440                 445
Ala Asn Thr Cys Arg Gln Asp Leu Thr Thr Thr Glu Glu Leu Pro Leu
                450                 455                 460
Glu Asn Asn Asn Phe Asn Leu Leu Ser His Val Thr Phe Leu Arg Phe
465                 470                 475                 480
Asn Thr Thr Gln Gly Gly Pro Leu Ala Thr Leu Gly Phe Val Pro Thr
                    485                 490                 495
Tyr Val Trp Thr Arg Glu Asp Val Asp Phe Thr Asn Thr Ile Thr Ala
                500                 505                 510
Asp Arg Ile Thr Gln Leu Pro Trp Val Lys Ala Ser Glu Ile Gly Gly
                515                 520                 525
Gly Thr Thr Val Val Lys Gly Pro Gly Phe Thr Gly Gly Asp Ile Leu
                530                 535                 540
Arg Arg Thr Asp Gly Gly Ala Val Gly Thr Ile Arg Ala Asn Val Asn
545                 550                 555                 560
Ala Pro Leu Thr Gln Gln Tyr Arg Ile Arg Leu Arg Tyr Ala Ser Thr
                    565                 570                 575
Thr Ser Phe Val Val Asn Leu Phe Val Asn Asn Ser Ala Ala Gly Phe
                580                 585                 590
Thr Leu Pro Ser Thr Met Ala Gln Asn Gly Ser Leu Thr Tyr Glu Ser
                595                 600                 605
Phe Asn Thr Leu Glu Val Thr His Thr Ile Arg Phe Ser Gln Ser Asp
                610                 615                 620
Thr Thr Leu Arg Leu Asn Ile Phe Pro Ser Ile Ser Gly Gln Glu Val
625                 630                 635                 640
Tyr Val Asp Lys Leu Glu Ile Val Pro Ile Asn Pro Thr Arg Glu
                    645                 650                 655
```

PLANT-OPTIMIZED GENES ENCODING PESTICIDAL TOXINS

CROSS-REFERENCE TO RELATED APPLICATIONS

The subject application claims priority to U.S. Provisional Patent Application Serial No. 60/065,215 (filed Nov. 12, 1997) and to U.S. Provisional Patent Application Serial No. 60/076,445 (filed Mar. 2, 1998).

BACKGROUND OF THE INVENTION

Insects and other pests cost farmers billions of dollars annually in crop losses and in the expense of keeping these pests under control. The losses caused by insect pests in agricultural production environments include decrease in crop yield, reduced crop quality, and increased harvesting costs.

Chemical pesticides have provided an effective method of pest control; however, the public has become concerned about the amount of residual chemicals which might be found in food, ground water, and the environment. Therefore, synthetic chemical pesticides are being increasingly scrutinized, and correctly so, for their potential toxic environmental consequences. Synthetic chemical pesticides can poison the soil and underlying aquifers, pollute surface waters as a result of runoff, and destroy non-target life forms. Synthetic chemical control agents have the further disadvantage of presenting public safety hazards when they are applied in areas where pets, farm animals, or children may come into contact with them. They may also provide health hazards to applicants, especially if the proper application techniques are not followed. Regulatory agencies around the world are restricting and/or banning the uses of many pesticides and particularly the synthetic chemical pesticides which are persistent in the environment and enter the food chain. Examples of widely used synthetic chemical pesticides include the organochlorines, e.g., DDT, mirex, kepone, lindane, aldrin, chlordane, aldicarb, and dieldrin; the organophosphates, e.g., chlorpyrifos, parathion, malathion, and diazinon; and carbamates. Stringent new restrictions on the use of pesticides and the elimination of some effective pesticides from the market place could limit economical and effective options for controlling costly pests.

Because of the problems associated with the use of synthetic chemical pesticides, there exists a clear need to limit the use of these agents and a need to identify alternative control agents. The replacement of synthetic chemical pesticides, or combination of these agents with biological pesticides, could reduce the levels of toxic chemicals in the environment.

A biological pesticidal agent that is enjoying increasing popularity is the soil microbe *Bacillus thuringiensis* (B.t.) The soil microbe *Bacillus thuringiensis* (B.t.) is a Gram-positive, spore-forming bacterium. Most strains of *B.t.* do not exhibit pesticidal activity. Some *B.t.* strains produce, and can be characterized by, parasporal crystalline protein inclusions. These "δ-endotoxins," which typically have specific pesticidal activity, are different from exotoxins, which have a non-specific host range. These inclusions often appear microscopically as distinctively shaped crystals. The proteins can be highly toxic to pests and are specific in their toxic activity.

Preparations of the spores and crystals of *B. thuringiensis* subsp. kurstaki have been used for many years as commercial insecticides for lepidopteran pests. For example, *B. thuringiensis* var. kurstaki HD-1 produces a crystalline δ-endotoxin which is toxic to the larvae of a number of lepidopteran insects.

The cloning and expression of a *B.t.* crystal protein gene in *Escherichia coli* was described in the published literature more than 15 years ago (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of *B.t.* crystal protein in *E. coli*. Recombinant DNA-based *B.t.* products have been produced and approved for use.

Commercial use of *B.t.* pesticides was originally restricted to a narrow range of lepidopteran(caterpillar)pests. More recently, however, investigators have discovered *B.t.* pesticides with specificities for a much broader range of pests. For example, other species of *B.t.*, namely israelensis and morrisoni (a.k.a. tenebrionis, a.k.a. *B.t.* M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255).

New subspecies of *B.t.* have now been identified, and genes responsible for active δ-endotoxin proteins have been isolated and sequenced (Höfte, H., H. R. Whiteley [1989] *Microbiological Reviews* 52(2):242–255). Höfte and Whiteley classified *B.t.* crystal protein genes into four major classes. The classes were cryI (Lepidoptera-specific), cryII (Lepidoptera- and Diptera-specific), cryIII (Coleoptera-specific), and cryIV (Diptera-specific). The discovery of strains specifically toxic to other pests has been reported (Feitelson, J. S., J. Payne, L. Kim [1992] *Bio/Technology* 10:271–275). For example, the designations CryV and CryVI have been proposed for two new groups of nematode-active toxins.

Many *Bacillus thuringiensis* δ-endotoxin crystal protein molecules are composed of two functional segments. For these proteins, the protease-resistant core toxin is the first segment and corresponds to about the first half of the protein molecule. The three-dimensional structure of a core segment of a CryIIIA *B.t.* δ-endotoxin is known, and it was proposed that all related toxins have that same overall structure (Li, J., J. Carroll, D. J. Ellar [1991] *Nature* 353:815–821). The second half of the molecule is often referred to as the "protoxin segment." The protoxin segment is believed to participate in toxin crystal formation (Arvidson,H., P. E. Dunn, S. Strand, A. I. Aronson [1989] *Molecular Microbiology* 3:1533–1534; Choma, C. T., W. K. Surewicz, P. R. Carey, M. Pozsgay, T. Raynor, H. Kaplan [1990] *Eur. J Biochem.* 189:523–527). The fill 130 kDa toxin molecule is typically processed to the resistant core segment by proteases in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J Biochem.* 156:531–540) or by reducing toxin solubility (Aronson, A. I., E. S. Han, W. McGaughey, D. Johnson [1991] *Appl. Environ. Microbiol.* 57:981–986).

The 1989 nomenclature and classification scheme of Höfte and Whiteley was based on both the deduced amino acid sequence and the host range of the toxin. That system was adapted to cover 14 different types of toxin genes which were divided into five major classes. The number of sequenced *Bacillus thuringiensis* crystal protein genes currently stands at more than 50. A revised nomenclature scheme has been proposed which is based solely on amino acid identity (Crickmoreet et al. [1996] Society for Invertebrate Pathology, 29th Annual Meeting, IIIrd International Colloquium on *Bacillus thuringiensis*, University of Cordoba, Cordoba, Spain, Sep. 1–6, 1996, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, although a number have been reclassified.

With the use of genetic engineering techniques, new approaches for delivering *B.t.* toxins to agricultural environments are under development, including the use of plants genetically engineered with *B.t.* toxin genes for insect resistance and the use of stabilized, microbial cells as delivery vehicles of *B.t.* toxins (Gaertner, F. H., L. Kim [1988] *TIBTECH* 6:S4-S7). Thus, isolated *B.t.* endotoxin genes are becoming commercially valuable.

Various improvements have been achieved by modifying *B.t.* toxins and/or their genes. For example, U.S. Pat. Nos. 5,380,831 and 5,567,862 relate to the production of synthetic insecticidal crystal protein genes having improved expression in plants.

Obstacles to the successful agricultural use of *B.t.* toxins include the development of resistance to *B.t.* toxins by insects. In addition, certain insects can be refractory to the effects of *B.t.* The latter includes insects such as boll weevil and black cutworm as well as adult insects of most species which heretofore have demonstrated no apparent significant sensitivity to *B.t.* δ-endotoxins.

Thus, resistance management strategies in *B.t.* plant technology have become of great interest, and there remains a great need for new toxin genes. As a result of extensive research and resource investment, other patents have issued for new *B.t.* isolates, toxins, and genes, and for new uses of *B.t.* isolates. See Feitelson et al, supra, for a review. Additional examples include the following:

| B.t. Isolate, Toxin, and/or Gene | Exemplified Pesticidal Activity of Toxin | U.S. Pat. No. (unless otherwise indicated) |
|---|---|---|
| PS81I, 81IA, 81IB2 | lepidopteran | 5,126,133; 5,188,960 |
| Cry1Ac | lepidopteran | Adang et al., GENBANK Acc. No. M11068 |
| IC/IA(b) chimeric toxin | lepidopteran | 5,593,881 |
| IF/IA(b) chimeric toxin | lepidopteran | 5,527,883 |
| PS158C, 158C2c | lepidopteran | 5,268,172; 5,723,758 |
| PS31G1, 31G1a | lepidopteran | WO 98/00546 (published PCT application) |

However, the discovery of new *B.t.* isolates and new uses of known *B.t.* isolates remains an empirical, unpredictable art.

There remains a great need for new toxin genes that can be successfully expressed at adequate levels in plants in a manner that will result in the effective control of insects and other pests.

SUMMARY OF THE INVENTION

The subject invention concerns materials and methods useful in the control of pests and, particularly, plant pests. More specifically, the subject invention provides plant-optimized polynucleotide sequences that encode pesticidal toxins (full-length and truncated). Truncated polynucleotide sequences can be used to produce truncated toxins or for the production of fusion (or chimeric) genes and proteins. The polynucleotide sequences of the subject invention have certain modifications, compared to wild-type sequences, that make them particularly well-suited for optimized expression in plants. Using techniques known to those skilled in the art, the polynucleotide sequences described herein can be used to transform plants in order to confer pest resistance upon said plants.

In one preferred embodiment, the subject invention provides plant-optimized polynucleotide sequences which encode Cry1F toxins that are active against lepidopteran insects. These polynucleotide sequences include plant-optimized genes designated 1F1AB-PO, 1F-T-PO, 1F-7G-PO, and 1F-7Z-PO.

The subject invention also provides other plant-optimized genes that encode other proteins that are toxic to pests. Preferred embodiments are referred to herein as 1AC1AB-N-PO, 1AC1AB-PO, 1AC1AB-B-PO, 1AC-T-PO, 1AC-TB-PO, 1AC-TBX-PO, 1C-T-PO, 1C1AB-PO, 158C2c-PO, 158C2c-T-PO, and 31G1a-PO.

The subject invention further provides plant-optimized polynucleotide sequences that encode C-terminal, protoxin portions that can be used with genes encoding truncated, core toxins to produce full-length toxins. Preferred embodiments of plant-optimized protoxins are designated PT-1AB-PO and PT-1AB-2-PO.

In addition, the subject invention provides unique amino acids sequences for pesticidal toxins. These toxins are encoded by the genes designated 1F1AB-PO; 1F-T-PO, 1F-7G-PO, and 1F-7Z-PO; 1AC1AB-N-PO, 1AC1AB-PO, and 1AC1AB-B-PO; 1C1AB-PO; 158C2c-PO; 158C2c-T-PO; and 31G1a-T-PO. Furthermore, the subject invention provides unique, C-terminal amino acid sequences for protoxin portions (of full-length *Bacillus thuringiensis* toxins) encoded by the polynucleotide sequences designated PT-1AB-PO and PT-1AB-2-PO.

BRIEF DESCRIPTION OF THE SEQUENCES

SEQ ID NO. 1 is a polynucleotide sequence for a full-length, plant-optimized cryIF/cryIA(b) hybrid gene designated 1F1AB-PO.

SEQ ID NO. 2 is an amino acid sequence for a full-length, plant-optimized CryIF/CryIA(b) chimeric toxin. The 1F1AB-PO gene encodes this toxin.

SEQ ID NO. 3 is a polynucleotide sequence for a truncated, plant-optimized cryIF gene designated 1F-T-PO.

SEQ ID NO. 4 is an amino acid sequence for a truncated, plant-optimized CryIF toxin. The genes designated 1F-T-PO, 1F-7G-PO, and 1F-7Z-PO encode this toxin.

SEQ ID NO. 5 is the native polynucleotide sequence of the wild-type, full length *B.t.* toxin gene designated 81IA (cryIF).

SEQ ID NO. 6 is the amino acid sequence of the full length, wild-type *B.t.* toxin designated 81IA (CryIF).

SEQ ID NO. 7 is a polynucleotide sequence for a gene designated 1F-7G-PO, which is optimized for expression in cotton.

SEQ ID NO. 8 is a polynucleotide sequence for a gene designated 1 F-7Z-PO, which is optimized for expression in maize.

SEQ ID NO. 9 is a polynucleotide sequence designated PT-1AB-PO, which is optimized for expression in plants. This gene, which encodes a Cry1Ab protoxin portion, can be used in conjunction with truncated genes (genes encoding truncated, core toxins) to make full-length toxins. Unless otherwise indicated, the chimeric genes exemplified herein are shown with this polynucleotide sequence (PT-1AB-PO).

SEQ ID NO. 10 is a polynucleotide sequence designated PT-1AB-2-PO, which is optimized for expression in cotton. This polynucleotide sequence is an alternative to PT-1AB-PO (and also encodes a Cry1Ab protoxin portion) and can also be used in conjunction with truncated genes (genes encoding truncated, core toxins) to make full-length toxins. PT-1AB-2-PO is preferred for use in a host that is transformed with more than one type of endotoxin transgene.

SEQ ID NO. 11 is an amino acid sequence of a protoxin portion encoded by the genes designated PT-1AB-PO and PT-1AB-2-PO.

SEQ ID NO. 12 is a polynucleotide sequence for a gene designated 1AC1AB-N-PO, which is optimized for expression in plants. This gene encodes a chimeric Cry1Ac (N-terminal)/Cry1Ab (protoxin) toxin.

SEQ ID NO. 13 is a polynucleotide sequence for a gene designated 1AC1AB-PO, which is optimized for expression in plants. This gene encodes a chimeric Cry1Ac (N-terminal)/Cry 1Ab (protoxin) toxin.

SEQ ID NO. 14 is a polynucleotide sequence for a gene designated 1AC1AB-B-PO, which is optimized for expression in plants. This gene encodes a chimeric Cry1Ac (N-terminal)/Cry1Ab (protoxin) toxin.

SEQ ID NO. 15 is an amino acid sequence of a toxin encoded by the genes designated 1AC1AB-N-PO, 1AC1AB-PO, and 1AC1AB-B-PO.

SEQ ID NO. 16 is a polynucleotide sequence for a gene designated 1AC-T-PO, which is optimized for expression in plants. This plant-optimized gene encodes a core toxin, the amino acid sequence of which is the same as that of the truncated form of a Cry1Ac toxin described by Adang et al. in *GENBANK* (Acc. No. M11068).

SEQ ID NO. 17 is a polynucleotide sequence for a gene designated 1AC-TB-PO, which is optimized for expression in plants. This plant-optimized gene encodes a core toxin, the amino acid sequence of which is the same as that of the truncated form of a Cry1Ac toxin described by Adang et al. in *GENBANK* (Acc. No. M11068).

SEQ ID NO. 18 is an alternative polynucleotide sequence for a gene designated 1AC-TBX-PO, which is optimized for expression in plants. This plant-optimized gene encodes a core toxin, the amino acid sequence of which is the same as that of the truncated form of a Cry1Ac toxin described by Adang et al. in *GENBANK* (Acc. No. M11068).

SEQ ID NO. 19 is a polynucleotide sequence, optimized for expression in dicots, for a gene designated 1C-T-PO, which encodes the truncated form of a Cry1C toxin designated 81IB2 in U.S. Pat. No. 5,246,852.

SEQ ID NO. 20 is a polynucleotide sequence for a gene designated 1C1AB-PO, which is optimized for expression in plants. This gene encodes a chimeric Cry1C (N-terminal)/Cry1Ab (protoxin) toxin.

SEQ ID NO. 21 is an amino acid sequence of a toxin encoded by the gene designated 1C1AB-PO.

SEQ ID NO. 22 is a polynucleotide sequence for a gene designated 158C2c-PO.

SEQ ID NO. 23 is an amino acid sequence for a full-length toxin encoded by the gene designated 158C2c-PO.

SEQ ID NO. 24 is a polynucleotide sequence for a gene designated 158C2c-T-PO.

SEQ ID NO. 25 is an amino acid sequence for a truncated toxin encoded by the gene designated 158C2c-T-PO.

SEQ ID NO. 26 is a polynucleotide sequence for a gene designated 31G1a-T-PO, which is optimized for expression in maize.

SEQ ID NO. 27 is an amino acid sequence for a truncated toxin encoded by the gene designated 31G1a-T-PO.

DETAILED DESCRIPTION OF THE INVENTION

The subject invention concerns materials and methods useful in the control of pests and, particularly, plant pests. More specifically, the subject invention provides plant-optimized polynucleotide sequences that encode pesticidal toxins (full-length and truncated). Truncated polynucleotide sequences can be used to produce truncated toxins or for the production of fusion (or chimeric) genes and proteins. The polynucleotide sequences of the subject invention have certain modifications, compared to wild-type sequences, that make them particularly well-suited for optimized expression in plants. Using techniques known to those skilled in the art, the polynucleotide sequences described herein can be used to transform plants in order to confer pest resistance upon said plants.

In one preferred embodiment, the subject invention provides plant-optimized polynucleotide sequences which encode Cryl F toxins that are active against lepidopteran insects. These polynucleotide sequences include plant-optimized genes designated 1F1AB-PO, 1F-T-PO, 1F-7G-PO, and 1F-7Z-PO.

The subject invention also provides other plant-optimized genes that encode other proteins that are toxic to pests. Preferred embodiments are referred to herein as 1AC1AB-N-PO, 1AC1AB-PO, 1AC1AB-B-PO, 1AC-T-PO, 1AC-TB-PO, 1AC-TBX-PO, 1C-T-PO, 1C1AB-PO, 158C2c-PO, 158C2c-T-PO, and 31G1a-PO.

The subject invention further provides plant-optimized polynucleotide sequences that encode C-terminal, protoxin portions that can be used with genes encoding truncated, core toxins to produce full-length toxins. Preferred embodiments of plant-optimized protoxins are designated PT-1AB-PO and PT-1AB-2-PO.

In addition, the subject invention provides unique amino acids sequences for pesticidal toxins. These toxins are encoded by the genes designated 1F1AB-PO; 1F-T-PO, 1F-7G-PO, and 1F-7Z-PO; 1AC1AB-N-PO, 1AC1AB-PO, and 1AC1AB-B-PO; 1C1AB-PO; 158C2c-PO; 158C2c-T-PO; and 31G1a-T-PO. Furthermore, the subject invention provides unique, C-terminal amino acid sequences for protoxin portions (of full-length *Bacillus thuringiensis* toxins) encoded by the polynucleotide sequences designated PT-1AB-PO and PT-1AB-2-PO.

In one embodiment the subject invention provides genes which express a CryIF toxin that is truncated compared to the full length CryIF toxin. The truncated toxins of the subject invention are typically missing all or a portion of the protoxin segment. Also, the truncated genes of the subject invention can be used for the production of fusion (or chimeric) genes and proteins. One example is the plant-optimized gene comprising a cryIF portion and a cryIA(b) portion, wherein the hybrid gene encodes a chimeric toxin. In a preferred embodiment, the CryIF portion of the chimeric toxin is itself pesticidal.

More specifically, one example of a chimeric DNA molecule of the subject invention is shown in SEQ ID NO. 1, which has a cryIF 5' portion and a 3' cryIA(b) portion of the DNA molecule. The chimeric toxin encoded by SEQ ID NO. 1 is shown in SEQ ID NO. 2. The chimeric toxin encoded by SEQ ID NO. 1 comprises a Cry1F core toxin comprising approximately the first 605 amino acids encoded by the nucleotides from approximately 1 to approximately 1815. This chimeric gene also comprises a cry1Ab protoxin portion, which encodes amino acids from approximately 606 to approximately 1148. The Cry1Ab protoxin portion is encoded by the nucleotides from approximately 1816 to approximately 3444.

The sequence of a preferred, truncated cryIF gene of the subject invention (1815 nucleotides) is shown in SEQ ID NO. 3. This truncated gene corresponds to nucleotides 1–1815 of the chimeric gene of SEQ ID NO. 1. A stop codon, such as TAA or TAG, can be added to this sequence at positions 1816–1818, for example, if the use of a truncated toxin, without a protoxin portion, is desired. Other polynucleotide sequences and genes of the subject invention can be similarly modified, as would be recognized by one skilled in the art. The synthetic, truncated Cry1F toxin (encodedby SEQ ID NO.3) is shown in SEQ ID NO.4.

As can be seen by comparing, for example, SEQ ID NOS. 1 and 2 with SEQ ID NOS. 3 and 4, and with SEQ ID NOS. 9 and 10, there can be some overlap between the sequences for the "truncated genes" and the sequences for the "protoxin portions" exemplified herein.

PT-1AB-PO can be used in preferred embodiments in combination with other truncated genes of the subject invention, such as the 1C-T-PO gene, in order to form other hybrid genes that encode full-length toxins. PT-1AB-2-PO (an alternative polynucleotide sequence that encodes a protoxin portion) can also be used with truncated genes (which are smaller than full-length toxin genes, so long as the protein encoded by the truncated gene retains pesticidal activity) to encode chimeric or hybrid toxins. Preferred uses of PT-1AB-2-PO are described above in the section entitled "Description of the Sequences."

Using techniques such as computer- or software-assisted sequence alignments, differences can be noted in the nucleotide sequence of the subject plant-optimized genes as compared to the wild-type genes or to previously known genes. For example, SEQ ID NO. 1 or SEQ ID NO 3 can be compared to SEQ ID NO 5, which is the 3522-basepair, wild-type cryIF gene. Similarly, differences in the unique amino acid sequences of the subject invention can be noted as compared to wild-type toxins or to previously known toxins.

It should be apparent to a person skilled in this art that, given the sequences of the genes as set forth herein, the genes of the subject invention can be obtained through several means. In preferred embodiments, the subject genes may be constructed synthetically by using a gene synthesizer, for example. The specific genes exemplified herein can also be obtained by modifying, according to the teachings of the subject invention, certain wild-type genes (for example, by point-mutation techniques) from certain isolates deposited at a culture depository as discussed below. For example, a wild-type cryIF gene can be obtained from B.t. isolate PS81I. Likewise, the cryIA(b) portions of the hybrid genes of the subject invention can be produced synthetically or can be derived by modifying wild-type genes. CryIA(b) toxins and genes have been described in, for example, Höfte et al. (1986) Eur. J Biochem. 161:273; Geiseret al (1986) Gene 48:109; and Haider et al. (1988) Nucleic Acids Res. 16:10927. Clones and additional wild-type isolates are discussed in more detail, above, in the section entitled "Background of the Invention" and in the list, below.

Cultures discussed in this application have been deposited in the Agricultural Research Service Patent Culture Collection (NRRL), Northern Regional Research Center, 1815 North University Street, Peoria, Ill. 61604, USA. The deposited strains listed below are disclosed in the patent references as discussed above in the section entitled "Background of the Invention."

| Subculture | Accession Number | Deposit Date |
| --- | --- | --- |
| B.t PS81I | NRRL B-18484 | April 19, 1989 |
| E. coli (NM522) (pMYC1603) (81IA) | NRRL B-18517 | June 30, 1989 |
| E. coli (NM522) (pMYC394) (81IB2) | NRRL B-18500 | May 17, 1989 |
| B.t PS158C2 | NRRL B-18872 | Sep. 17, 1991 |
| E. coli (NM522) (pMYC2383) (158C2c) | NRRL B-21428 | April 11, 1995 |
| B.t. PS31G1 | NRRL B-21560 | May 2, 1996 |
| E. coli (NM522) (pMYC2454) (31G1a) | NRRL B-21796 | June 27, 1997 |

It should be understood that the availability of a deposit does not constitute a license to practice the subject invention in derogation of patent rights granted by governmental action.

Genes and toxins. The polynucleotides of the subject invention can be used to form complete "genes" to encode proteins or peptides in a desired host cell. For example, as the skilled artisan would readily recognize, the polynucleotides of the subject invention are shown without stop codons. Also, the subject polynucleotides can be appropriately placed under the control of a promoter in a host of interest, as is readily known in the art.

As the skilled artisan would readily recognize, DNA can exist in a double-stranded form. In this arrangement, one strand is complementary to the other strand and vice versa. The "coding strand" is often used in the art to refer to the strand having a series of codons (a codon is three nucleotides that can be read three-at-a-time to yield a particular amino acid) that can be read as an open reading frame (ORF) to form a protein or peptide of interest. In order to express a protein in vivo, a strand of DNA is typically translated into a complementary strand of RNA which is used as the template for the protein. As DNA is replicated in a plant (for example) additional, complementary strands of DNA are produced. Thus, the subject invention includes the use of either the exemplified polynucleotides shown in the attached sequence listing or the complementary strands. RNA and PNA (peptide nucleic acids) that are functionally equivalent to the exemplified DNA are included in the subject invention.

Certain DNA sequences of the subject invention have been specifically exemplified herein. These sequences are exemplary of the subject invention. It should be readily apparent that the subject invention includes not only the genes and sequences specifically exemplified herein but also equivalents and variants thereof (such as mutants, fusions, chimerics, truncations, fragments, and smaller genes) that exhibit the same or similar characteristics relating to expressing toxins in plants, as compared to those specifically disclosed herein. As used herein, "variants" and "equivalents" refer to sequences which have nucleotide (or amino acid) substitutions, deletions (internal and/or terminal), additions, or insertions which do not materially affect the expression of the subject genes, and the resultant pesticidal activity, in plants. Fragments retaining pesticidal activity are also included in this definition. Thus, polynucleotides that are smaller than those specifically exemplified are included in the subject invention, so long as the polynucleotide encodes a pesticidal toxin.

Genes can be modified, and variations of genes may be readily constructed, using standard techniques. For example, techniques for making point mutations are well known in the art. In addition, commercially available exonucleases or endonucleases can be used according to standard procedures, and enzymes such as Bal31 or site-directed mutagenesis can be used to systematically cut off nucleotides from the ends of these genes. Useful genes can also be obtained using a variety of restriction enzymes.

It should be noted that equivalent genes will encode toxins that have high amino acid identity or homology with the toxins encoded by the subject genes. The amino acid homology will be highest in critical regions of the toxin which account for biological activity or are involved in the determination of three-dimensional configuration which ultimately is responsible for the biological activity. In this regard, certain substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the ability of plants to express the subject DNA sequences or from the biological activity of the toxin.

As used herein, reference to "isolated" polynucleotides and/or "purified" toxins refers to these molecules when they are not associated with the other molecules with which they would be found in nature and would include their use in plants. Thus, reference to "isolated and purified" signifies the involvement of the "hand of man" as described herein.

Recombinant hosts. The toxin-encoding genes of the subject invention can be introduced into a wide variety of microbial or plant hosts. In some embodiments of the subject invention, transformed microbial hosts can be used in preliminary steps for preparing precursors, for example, that will eventually be used to transform, in preferred embodiments, plant cells and plants so that they express the toxins encoded by the genes of the subject invention. Microbes transformed and used in this manner are within the scope of the subject invention. Recombinant microbes may be, for example, *B.t., E. coli,* or Pseudomonas. Transformations can be made by those skilled in the art using standard techniques. Materials necessary for these transformations are disclosed herein or are otherwise readily available to the skilled artisan.

Thus, in preferred embodiments, expression of the toxin gene results, directly or indirectly, in the intracellular production and maintenance of the pesticide. When transformed plants are ingested by the pest, the pests will ingest the toxin. The result is a control of the pest.

The *B.t.* toxin gene can be introduced via a suitable vector into a host, preferably a plant host. There are many crops of interest, such as corn, wheat, rice, cotton, soybeans, and sunflowers. The genes of the subject invention are particularly well suited for providing stable maintenance and expression, in the transformed plant, of the gene expressing the polypeptide pesticide, and, desirably, provide for improved protection of the pesticide from environmental degradation and inactivation.

While the subject invention provides specific embodiments of synthetic genes, other genes that are functionally equivalent to the genes exemplified herein can also be used to transform hosts, preferably plant hosts. Additional guidance for the production of synthetic genes can be found in, for example, U.S. Pat. No. 5,380,831.

All of the references cited herein are hereby incorporated by reference.

Following is an example which illustrates procedures for practicing the invention. This example should not be construed as limiting.

EXAMPLE 1

Insertion of Toxin Genes Into Plants

One aspect of the subject invention is the transformation of plants with the subject polynucleotide sequences encoding insecticidal toxins. The transformed plants are resistant to attack by the target pest. The genes of the subject invention are optimized for use in plants.

Obviously, a promoter region capable of expressing the gene in a plant is needed. Thus, for in planta expression, the DNA of the subject invention is under the control of an appropriate promoter region. Techniques for obtaining in planta expression by using such constructs is known in the art.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids.

Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516; Hoekema (1985) In: *The Binary Plant Vector System*, Offset-durkkerij Kanters B.V., Alblasserdam, Chapter 5; Fraley et al., *Crit. Rev. Plant Sci*. 4:1–46; and An et al (1985) *EMBOJ* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters etal. [1978] *MoL Gen. Genet*. 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivatedcells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A polynucleotide sequence optimized for expression in a plant wherein said polynucleotide sequence comprises a sequence selected from the group consisting of SEQ ID NO:1, SEQ ID NO:3, SEQ ID NO:14, and SEQ ID NO:26.

2. The polynucleotide according to claim 1 wherein said sequence is SEQ ID NO:1.

3. The polynucleotide according to claim 1 wherein said sequence is SEQ ID NO:3.

4. The polynucleotide according to claim 1 wherein said sequence is SEQ ID NO:14.

5. The polynucleotide according to claim 1 wherein said sequence is SEQ ID NO:26.

6. A DNA construct that comprises a polynucleotide and a promoter region active in a plant cell, wherein said promoter region is operatively linked to said polynucleotide and said polynucleotide is under the control of said promoter region, and wherein said polynucleotide comprises a sequence selected from the group consisting of SEQ ID NO:1, SEQ ID NO:3, SEQ ID NO:14, and SEQ ID NO:26.

7. The DNA construct according to claim 6 wherein said sequence is SEQ ID NO:1.

8. The DNA construct according to claim 6 wherein said sequence is SEQ ID NO:3.

9. The DNA construct according to claim 6 wherein said sequence is SEQ ID NO:14.

10. The DNA construct according to claim 6 wherein said sequence is SEQ ID NO:26.

11. A cell comprising a plant-optimized polynucleotide selected from the group consisting of SEQ ID NO:1, SEQ ID NO:3, SEQ ID NO:14, and SEQ ID NO:26; wherein said cell is selected from the group consisting of a plant cell and a microbial cell.

12. The cell according to claim 11 wherein said cell is a plant cell and said polynucleotide is SEQ ID NO:1.

13. The cell according to claim 11 wherein said cell is a plant cell and said polynucleotide is SEQ ID NO:3.

14. The cell according to claim 11 wherein said cell is a plant cell and said polynucleotide is SEQ ID NO:14.

15. The cell according to claim 11 wherein said cell is a plant cell and said polynucleotide is SEQ ID NO:26.

16. The cell according to claim 15 wherein said plant cell is a maize plant cell.

17. A method of producing transgenic plant cells wherein said method comprises transforming a plant cell with a polynucleotide comprising a sequence selected from the group consisting of SEQ ID NO:1, SEQ ID NO:3, SEQ ID NO:14, and SEQ ID NO:26; and culturing said plant cell under conditions whereby descendent generations of transgenic plant cells are produced.

* * * * *

UNITED STATES PATENT AND TRADEMARK OFFICE
CERTIFICATE OF CORRECTION

PATENT NO. : 6,218,188 B1
DATED : April 17, 2001
INVENTOR(S) : Guy A. Cardineau, Steven J. Stelman, Kenneth E. Narva It is certified that error appears in the above-identified patent and that said Letters Patent is hereby corrected as shown below:

Title page,
ABSTRACT, "lengthand" should be -- length and --.

Column 1,
Line 54, "(B.t.)" should be -- (B.t.). --.
Line 62, "microscopicallyas" should be -- microscopically as --.

Column 2,
Line 13, "lepidopteran(caterpillar)pests." should be -- lepidopteran (caterpillar) pests. --.
Line 51, "fill" should be -- full --.
Line 58, "J. Biochem." should be -- J. Biochem. --.
Lines 62-63, "H öfte" should be -- Höfte --.

Column 3,
Line 3, "(Crickmoreet et al." should be -- (Crickmore et al. --.

Column 4,
Line 63, "1 F-7Z-PO" should be -- 1F-7Z-PO --.

Column 6,
Line 28, "Cry1 F" should be -- Cry1F --.

Column 7,
Line 22, "encodedby" should be -- encoded by --.
Line 45, "SEQ ID NO 5" should be -- SEQ ID NO. 5 --.
Line 65, "J Biochem." should be -- J. Biochem. --.
Line 66, "Geiseret al" should be -- Geiser et al. --.

Column 11,
Line 10, "EMBOJ" should be -- EMBO J. --.

Column 12,
Line 6, "Holsters etal." should be -- Holsters et al. --.
Line 6, "MoL" should be -- Mol. --.

UNITED STATES PATENT AND TRADEMARK OFFICE
CERTIFICATE OF CORRECTION

PATENT NO.     : 6,218,188 B1
DATED          : April 17, 2001
INVENTOR(S)    : Guy A. Cardineau, Steven J. Stelman, Kenneth E. Narva It is certified that error appears in the above-identified patent and that said Letters Patent is hereby corrected as shown below:

<u>Column 95,</u>
Line 56, "polynucleotide sequence optimized" should be -- polynucleotide optimized --.
Line 57, "polynucleotide sequence comprises" should be -- polynucleotide comprises --.

Signed and Sealed this

Twenty-sixth Day of March, 2002

Attest:

*Attesting Officer*

JAMES E. ROGAN
*Director of the United States Patent and Trademark Office*